United States Patent
Mickle et al.

(10) Patent No.: US 9,259,364 B2
(45) Date of Patent: Feb. 16, 2016

(54) PACKAGE OF FOLDED DISPOSABLE ABSORBENT PANTS

(71) Applicant: Kimberly-Clark Worldwide, Inc., Neenah, WI (US)

(72) Inventors: Patrick James Mickle, Appleton, WI (US); Sara Elaine Welch, Chicago, IL (US); Joseph Andrew Mlinar, Appleton, WI (US); Timothy John Kettenhofen, Appleton, WI (US); Erica Faye Creighton, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/104,767

(22) Filed: Dec. 12, 2013

(65) Prior Publication Data

US 2015/0164711 A1 Jun. 18, 2015

(51) Int. Cl.
*B65D 25/54* (2006.01)
*A61F 13/551* (2006.01)
*B65D 5/42* (2006.01)

(52) U.S. Cl.
CPC ....... *A61F 13/5511* (2013.01); *A61F 13/55115* (2013.01); *B65D 5/4204* (2013.01); *B65D 25/54* (2013.01); *B65D 2201/00* (2013.01)

(58) Field of Classification Search
CPC ... A61F 13/5511; A61F 15/00; A61F 15/001; B65D 5/4204; B65D 5/528; B65D 5/5286; B65D 81/025
USPC ................. 206/438, 440, 494, 730, 733, 734, 206/775–779; 604/385.01, 385.02
See application file for complete search history.

(56) References Cited

U.S. PATENT DOCUMENTS

| | | | |
|---|---|---|---|
| 3,963,029 | A | 6/1976 | Brooks |
| 3,978,861 | A | 9/1976 | Schaar |
| 4,802,884 | A | 2/1989 | Froeidh et al. |
| H1376 | H | 11/1994 | Osborn, III et al. |
| 5,449,353 | A | 9/1995 | Watanabe et al. |
| 5,599,339 | A | 2/1997 | Horney |
| 5,624,424 | A | 4/1997 | Saisaka et al. |
| 5,745,922 | A | 5/1998 | Rajala et al. |
| 5,853,404 | A | 12/1998 | Schmitz |
| 5,940,887 | A | 8/1999 | Rajala et al. |
| 6,132,410 | A | 10/2000 | Van Gompel et al. |
| 6,240,569 | B1 | 6/2001 | Van Gompel et al. |
| 6,312,420 | B1 | 11/2001 | Sasaki et al. |
| 6,626,881 | B2 | 9/2003 | Shingu et al. |

(Continued)

FOREIGN PATENT DOCUMENTS

| | | | | |
|---|---|---|---|---|
| EP | 0 865 780 A2 | 9/1998 | | |
| JP | WO 2014104215 A1 | * | 7/2014 | .......... A61F 13/5511 |

*Primary Examiner* — Bryon Gehman
(74) *Attorney, Agent, or Firm* — Kimberly-Clark Worldwide, Inc.

(57) ABSTRACT

A package of folded absorbent pants includes a housing portion with a front wall having a transparent window region. A plurality of absorbent pants are disposed within the housing portion. At least one of the pants is a display pant having a first folded configuration and being positioned within the housing portion to be at least partially visible through the transparent window region. A portion of the pants have a second folded configuration and are aligned in facing relation to define a first stack. The display pant is positioned within the housing portion such that the longitudinal direction of the display pant is aligned in a first direction and the first stack longitudinal direction is aligned in a second direction that is different than the first direction.

20 Claims, 23 Drawing Sheets

(56) References Cited

U.S. PATENT DOCUMENTS

| | | |
|---|---|---|
| 6,702,798 B2 | 3/2004 | Christoffel et al. |
| 7,604,624 B2 | 10/2009 | Veith et al. |
| 8,261,914 B2 | 9/2012 | Hooyman et al. |
| 8,317,022 B2 | 11/2012 | Hagner et al. |
| 8,459,457 B2 | 6/2013 | Hagner et al. |
| 2003/0055389 A1 | 3/2003 | Sanders et al. |
| 2004/0116887 A1 | 6/2004 | Thorson et al. |
| 2004/0167489 A1 | 8/2004 | Kellenberger et al. |
| 2008/0134487 A1 | 6/2008 | Hartono |

* cited by examiner

PACKAGE OF FOLDED DISPOSABLE ABSORBENT PANTS

BACKGROUND OF THE INVENTION

People rely on disposable absorbent garments in their everyday lives, including such garments as adult incontinence products, enuresis pants, training pants, and diapers. Many manufacturers seek to better meet the needs of users of such products. With certain products, such as adult incontinence underwear and enuresis pants, it is important that the garments look and feel as much as possible like "regular" underwear to promote an improved sense of normalcy to the wearer who suffers from incontinence or enuresis. Thus, there is a need for a package of incontinence or enuresis underwear that better resembles a package of durable underwear so as to improve the feeling of normalcy for the purchaser/user. There is also a need for a package of incontinence or enuresis underwear that allows the potential purchaser to see selected features of the underwear, such as, for example, cloth-like material used to make the underwear and elastic waistbands.

SUMMARY OF THE INVENTION

In one aspect, a package of folded absorbent pants includes a housing portion which defines a height dimension, a width dimension, and a depth dimension. The housing portion includes a front wall and a back wall, each of which extends along the width and height dimensions. The front wall is spaced from the back wall in the depth dimension. The front wall includes a transparent window region. A plurality of absorbent pants are disposed within the housing portion. Each pant defines a waist opening, two leg openings, a waist end, and a crotch end. Each pant defines a pant longitudinal direction that extends from the waist end to the crotch end and a pant transverse direction that is perpendicular to the longitudinal direction. At least one of the pants is a display pant having a first folded configuration and being positioned within the housing portion to be at least partially visible through the transparent window region. A portion of the pants are aligned in facing relation to define a first stack. Each pant in the first stack has a second folded configuration and the longitudinal direction of each pant in the first stack is aligned to define a first stack longitudinal direction. The display pant is positioned within the housing portion such that the longitudinal direction of the display pant is aligned in a first direction and the first stack longitudinal direction is aligned in a second direction that is different than the first direction.

In some embodiments, the front wall includes text which defines a reading direction aligned with the first stack longitudinal direction and perpendicular to the display pant longitudinal direction.

In some embodiments, the first folded configuration is different than the second folded configuration.

In some embodiments, the display pant defines a first folded area in the first folded configuration and each pant in the first stack defines a second folded area in the second folded configuration that is larger than the first folded area.

In some embodiments, the display pant further defines a waistband region which abuts the waist end and which extends in the transverse direction to at least partially encircle the waist opening. At least a portion of the waistband region is visible through the transparent window region.

In some embodiments, the pants in the first stack are oriented within the housing portion such that the plane defined by the longitudinal direction and the lateral direction of the pants in the first stack is parallel with the front wall.

In some embodiments, a portion of the pants are aligned in facing relation to define a second stack and each pant in the second stack has a third folded configuration and the longitudinal direction of each pant in the second stack is aligned to define a second stack longitudinal direction. In some embodiments, at least one of the pants is a second display pant having a fourth folded configuration and being positioned within the housing portion to be at least partially visible through the transparent window region. In some embodiments, the transparent window region includes a first window and a second window. The first window is separated from the second window by an opaque bridge and the first display pant is positioned within the housing portion to be at least partially visible through the first window and the second display pant is positioned within the housing portion to be at least partially visible through the second window.

In another aspect, the present invention provides a package of folded absorbent pants. The package includes a housing portion which defines a height dimension, a width dimension, and a depth dimension. The housing portion includes a front wall and a back wall, each of which extends along the width and height dimensions. The front wall being spaced from the back wall in the depth dimension. The front wall includes a transparent window region. A plurality of absorbent pants are disposed within the housing portion. Each pant defines a waist opening, two leg openings, a waist end, and a crotch end. Each pant defines a pant longitudinal direction that extends from the waist end to the crotch end and a pant transverse direction that is perpendicular to the longitudinal direction. Each pant defines a waistband region which abuts the waist end and which extends in the transverse direction to at least partially encircle the waist opening. At least one of the pants is a first display pant having a first folded configuration and being positioned within the housing portion such that the waistband region is at least partially visible through the transparent window region. At least one of the pants is a second display pant having a second folded configuration and being positioned within the housing portion to be at least partially visible through the transparent window region but the waistband region is not visible through the transparent window region. A portion of the pants are aligned in facing relation to define a first stack. Each pant in the first stack has a third folded configuration and the longitudinal direction of each pant in the first stack is aligned to define a first stack longitudinal direction. A portion of the pants are aligned in facing relation to define a second stack. Each pant in the second stack has a fourth folded configuration. The longitudinal direction of each pant in the second stack is aligned to define a second stack longitudinal direction. The first display pant and the second display pant are positioned within the housing portion such that the longitudinal direction of the first display pant is aligned with a first direction, the longitudinal direction of the second display pant is aligned with a second direction that is different than the first direction, and the longitudinal direction of the first stack is aligned with the second direction.

In various embodiments, the front wall includes text which defines a reading direction aligned with the first stack longitudinal direction and the second display pant longitudinal direction and perpendicular to the first display pant longitudinal direction.

In various embodiments, the first folded configuration is the same as the second folded configuration and different than the third folded configuration.

In various embodiments, the second folded configuration is the same as the third folded configuration and different than the first folded configuration.

In various embodiments, the first display pant defines a first folded area in the first folded configuration and the second display pant defines a second folded area in the second folded configuration that is larger than the first folded area.

In various embodiments, the pants in the first stack are positioned such that the plane defined by the longitudinal direction and the lateral direction is parallel with the front wall and the pants in the second stack are positioned such that the plane defined by the longitudinal direction and the lateral direction is parallel with the front wall.

In various embodiments, the first display pant overlays the first stack and the second display pant overlays the second stack.

In various embodiments, the transparent window region includes a first window and a second window. The first window is separated from the second window by an opaque bridge. The first display pant is positioned within the housing portion to be at least partially visible through the first window and the second display pant is positioned within the housing portion to be at least partially visible through the second window.

In various embodiments, the first display pant has a first color and the second display pant has a second color different than the first color.

In another aspect, the present invention provides a package of folded absorbent pants. The package includes a housing portion which defines a height dimension, a width dimension, and a depth dimension. The housing portion includes a front wall and a back wall, each of which extends along the width and height dimensions. The front wall being spaced from the back wall in the depth dimension. The front wall includes a transparent window region. The front wall also includes text that defines a reading direction that is aligned with the width dimension of the housing portion. A plurality of absorbent pants are disposed within the housing portion. Each pant defining a waist opening, two leg openings, a waist end, and a crotch end. Each pant defining a pant longitudinal direction that extends from the waist end to the crotch end and a pant transverse direction that is perpendicular to the longitudinal direction. Each pant further defining a waistband region which abuts the waist end and which extends in the transverse direction to at least partially encircle the waist opening. At least one of the pants is a first display pant having a first folded configuration and being positioned within the housing portion to be at least partially visible through the transparent window region. At least one of the pants is a second display pant having a second folded configuration and being positioned within the housing portion to be at least partially visible through the transparent window region. A portion of the pants are aligned in facing relation to define a first stack. Each pant in the first stack has a third folded configuration and the longitudinal direction of each pant in the first stack is aligned to define a first stack longitudinal direction. A portion of the pants are aligned in facing relation to define a second stack. Each pant in the second stack has a fourth folded configuration and the longitudinal direction of each pant in the second stack is aligned to define a second stack longitudinal direction. The first display pant and the second display pant are positioned within the housing portion such that the longitudinal direction of the first display pant is aligned with a first direction, the longitudinal direction of the second display pant is aligned with a second direction that is different than the first direction. The longitudinal direction of the first stack is aligned with the second direction and the longitudinal direction of the second stack is aligned with the second direction. The first folded configuration is different than the second folded configuration, the third folded configuration, and the fourth folded configuration.

In various embodiments, the first display pant is positioned within the housing portion such that the waistband region is at least partially visible through the transparent window region and the second display pant is positioned within the housing portion such that the waistband region is not visible through the transparent window region.

DEFINITIONS

Figure 1:
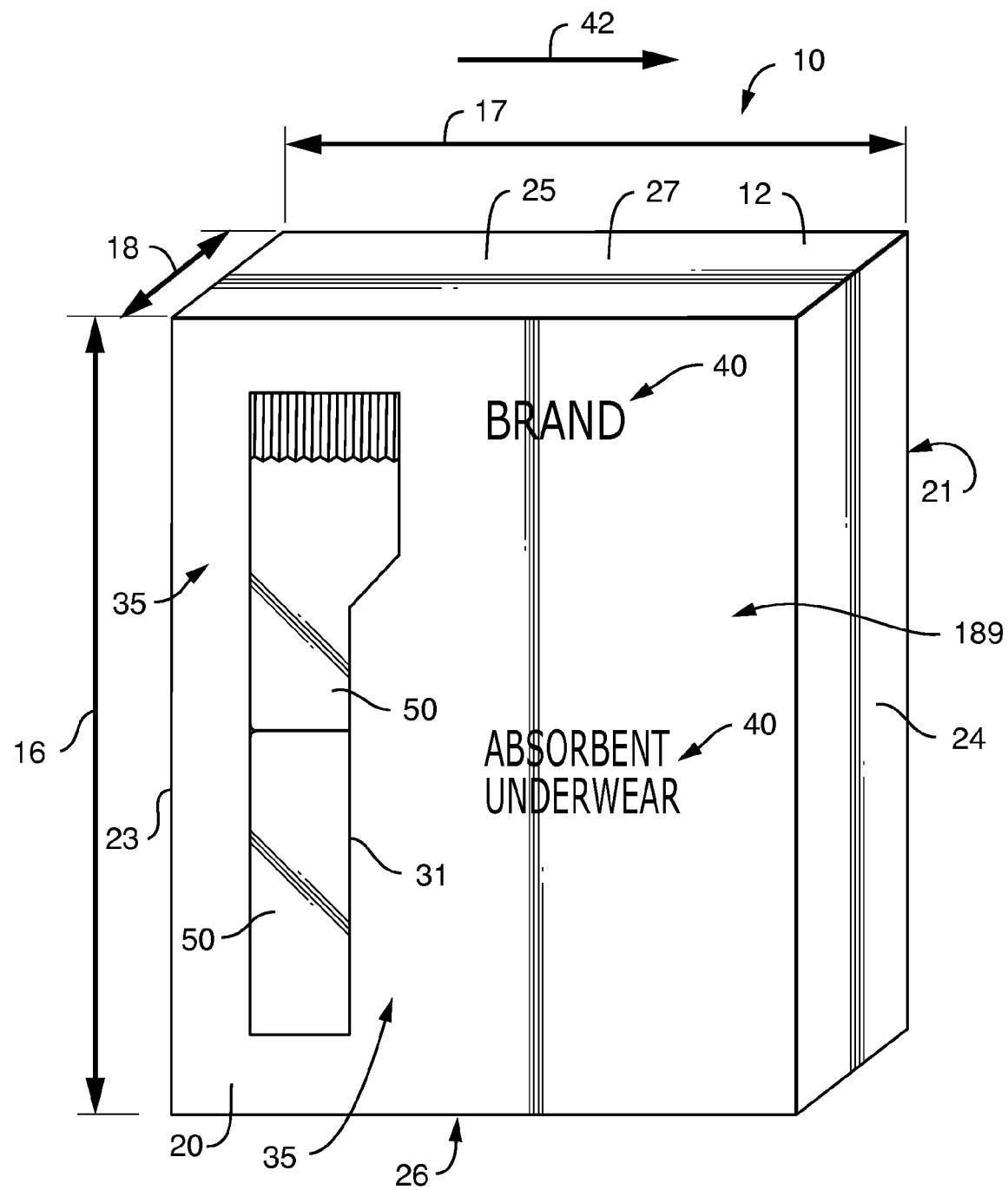
FIG. 1 representatively illustrates a perspective view of an exemplary package of folded disposable absorbent pants.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

"Integral" is used to refer to various portions of a single unitary element rather than separate structures bonded to or placed with or placed near one another.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis.

These terms may be defined with additional language in the remaining portions of the specification.

DETAILED DESCRIPTION OF THE DRAWINGS

Reference to the Figures shall be made in describing various aspects and embodiments of the invention. It should be noted that the embodiments depicted in the Figures and described herein are merely representative examples of the pants and package of the invention. The various aspects and embodiments of the present invention are suitable for use with adult incontinence pants, prefastened disposable diapers, disposable swim pants, disposable training pants, disposable enuresis garments, and the like.

Figure 2:
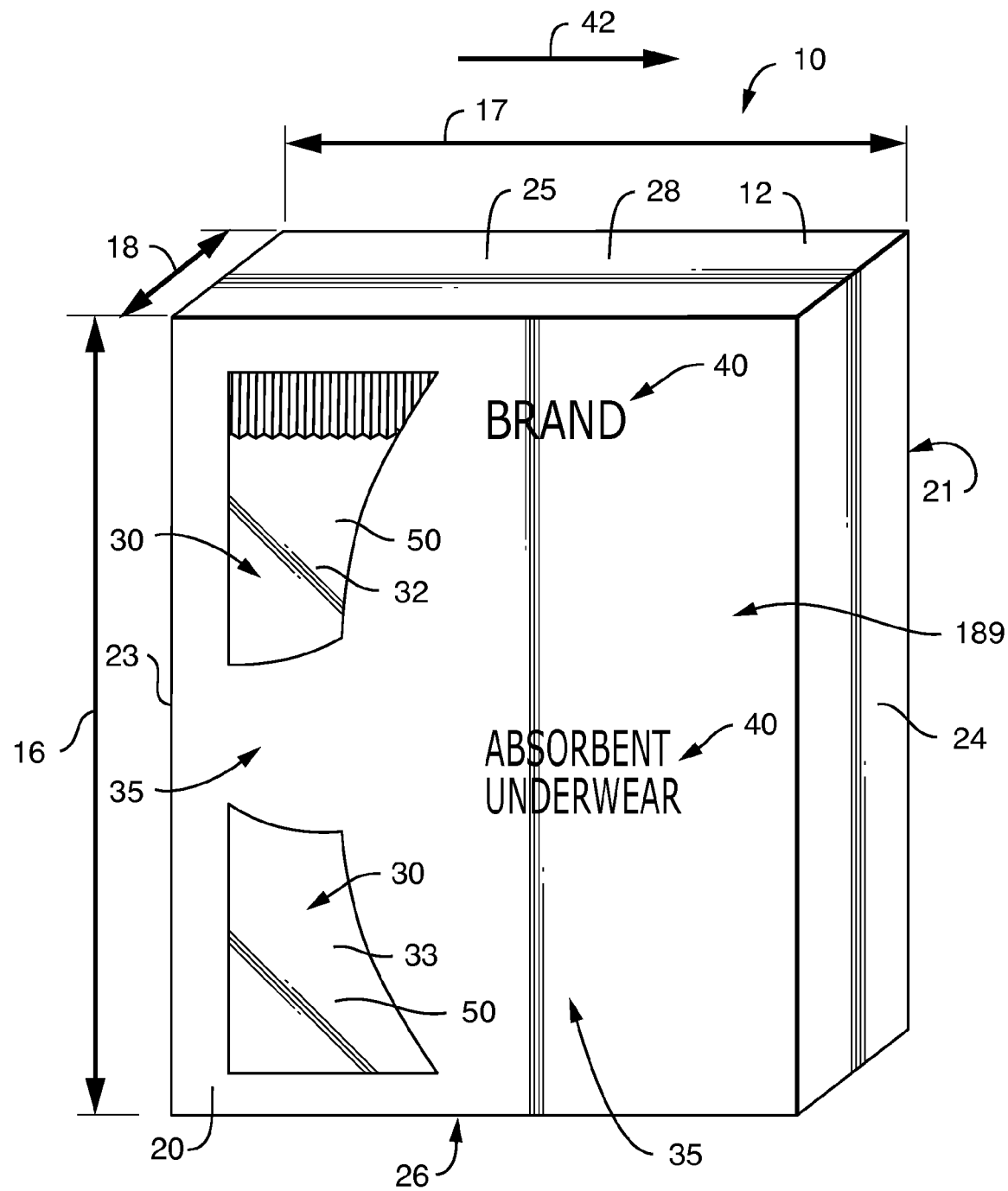
FIG. 2 representatively illustrates a perspective view of another exemplary package of folded disposable absorbent pants.

Referring to FIGS. 1 and 2, the invention relates to a package 10 of folded disposable absorbent pants 50. The package includes a housing portion 12. The housing portion 12 houses or contains the pants 50 by partially or completely forming an enclosure around the pants 50. The housing portion 12 defines a height dimension 16, a width dimension 17, and a depth dimension 18. The housing portion 12 includes a front wall 20 and a back wall 21, each of which extends along the height dimension 16 and the width dimension 17. The front wall 20 is spaced from the back wall 21 in the depth dimension 18. In particular embodiments, the housing portion 12 also includes a first side wall 23 and a second side wall 24, each of which extends along the height dimension 16 and the depth dimension 18. The first side wall 23 is spaced from the second side wall 24 in the width dimension 17. In particular embodiments, the housing portion 12 also includes a top wall 25 and a bottom wall 26, each of which extends along the width dimension 17 and the depth dimension 18. The top wall 25 is spaced from the bottom wall 26 in the height dimension 16.

The housing portion 12 of the package 10 may be formed of any suitable packaging material, such as, for example, plastic film, paperboard, corrugated board, flexible polymeric material, semi-rigid plastic, or combinations thereof. In some embodiments, the housing portion comprises, at least in part, a carton 27, such as a paperboard carton as illustrated in FIG. 1. In some embodiments, the housing portion may comprise a plastic bag 28 as illustrated in FIG. 2. The housing portion may optionally include one or more inserts disposed within the housing portion, such as a paperboard insert. Additional details regarding suitable housing configurations, materials, inserts, and the like are disclosed in more detail in U.S. Pat.

No. 8,317,022 to Hagner et al. and U.S. Pat. No. 8,261,914 to Hooyman et al, the entirety of each is incorporated herein by reference where not contradictory.

The front wall 20 includes a transparent window region 30 and an opaque border region 35. As described further below, the transparent window region is desirably configured to allow a consumer to view one or more portions of one or more pants 50 disposed within the package 10, while the opaque border region is configured to obscure or block from view one or more portions of one or more pants disposed within the package 10.

The transparent window region 30 may be provided by any mechanism which allows a consumer to see through the front wall 20 into the interior of the housing portion 12. For example, in an embodiment in which the housing portion 12 comprises a carton, the transparent window region 30 can comprise an opening 31 in the carton 27, as illustrated in FIG. 1. The opening 31 can be covered or sealed with a flexible or stiff translucent or transparent plastic material, or can be left uncovered and unsealed. If the entire carton is constructed of a plastic material, such as a semi-rigid plastic material, the window region can comprise a transparent or translucent portion of the carton (not illustrated). In another example, where the housing portion 12 comprises a bag 28, such as a plastic bag, the transparent window region 30 is defined by a transparent portion of the bag, as representatively illustrated in FIG. 2.

The opaque border region 35 may be provided by any mechanism which obscures or blocks from view one or more portions of one or more pants 50 disposed within the package 10. In embodiments in which the housing portion comprises a carton 27, such as a paperboard carton, the opaque border region 35 can be defined by a portion of the carton 27. For example, in the embodiment depicted in FIG. 1, in which the housing portion 12 comprises a paperboard carton 27, the opaque border region 35 comprises paperboard. If the entire carton is constructed of a plastic material, such as a semi-rigid plastic material or a flexible plastic bag, the opaque border region can comprise an opaque insert, such as a paperboard insert, which is positioned within the housing portion (not illustrated). In another version where the housing portion 12 is constructed of a plastic material, such as a semi-rigid plastic material or a flexible plastic bag 28, the opaque border region 35 can comprise an opaque material, such as printed ink, coated onto the carton or bag as illustrated in FIG. 2.

The shape and size of the transparent window region 30 and of the opaque border region 35 may vary. For example, the opaque border region 35 may partially or fully border the transparent window region 30 on one or more sides of the transparent window region 30. In the example representatively illustrated in FIG. 1, the opaque border region 35 fully borders the transparent window region 30 on all four sides (that is, completely surrounds the transparent window region 30). In other embodiments, the housing portion may include a C-shaped opaque, paperboard insert which partially obscures the front wall, the back wall, the top wall, and/or the bottom wall, such that the insert defines the transparent window region. In other embodiments, the opaque border region 35 may fully border the transparent window region 30 on all sides and may also subdivide the transparent window region 30 into a first window 32 and a second window 33 as illustrated in FIG. 2. The first window 32 and/or the second window 33 are configured to allow a consumer to view one or more portions of one or more pants 50 disposed within the package 10.

Desirably, printed text 40 is disposed on or near the front wall 20. For example, the printed text 40 can be printed on an outer surface of the housing portion 12, or on a surface of an insert. The printed text 40 is aligned in a reading direction 42. "Reading direction" means the direction in which the printed text reads, such as left-to-right in languages that employ the Roman alphabet. In particular embodiments, such as those representatively illustrated in FIGS. 1 and 2, the printed text 40 is oriented such that the reading direction 42 is aligned with the width dimension 17. In such embodiments, the reading direction 42 is perpendicular to both the height dimension 16 as well as to the longitudinal direction 51 of each pant 50 within the package 10.

Figure 3:
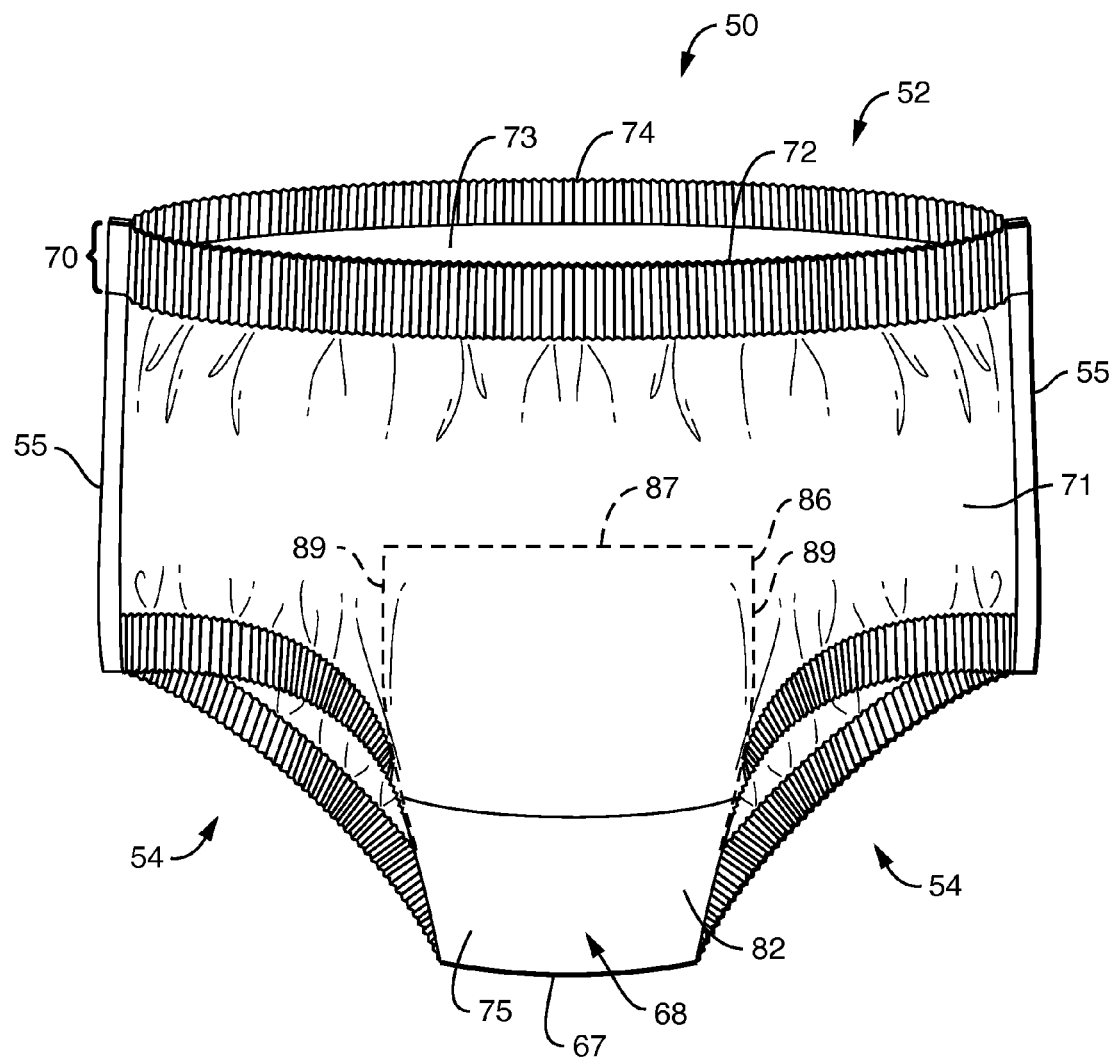
FIG. 3 representatively illustrates a front perspective view of an exemplary disposable absorbent pant.
Figure 4:
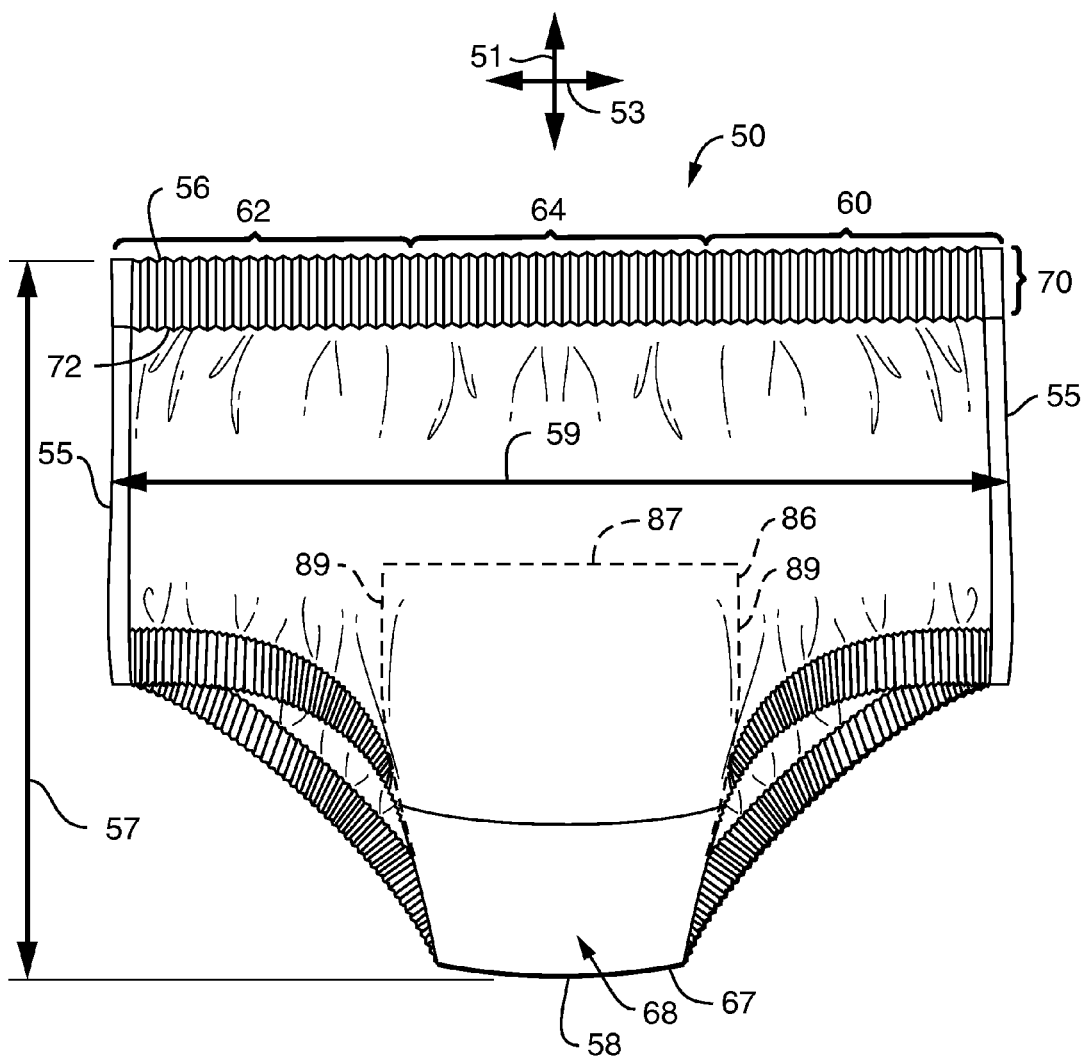
FIG. 4 representatively illustrates a front plan view of the disposable absorbent pant of FIG. 3.

The package 10 further includes a plurality of disposable absorbent pants disposed within the housing portion 12. Referring now to FIGS. 3 and 4, an exemplary pant 50 is illustrated in a front perspective view and a front plan view respectively. Each pant 50 defines a waist opening 52, two leg openings 54, a waist end 56, and a crotch end 58. In particular embodiments, each pant includes two side seams 55 which join the front portion of the pant to the back portion. Each pant defines a longitudinal direction 51 that extends from the waist end 56 to the crotch end 58, and each pant defines a transverse direction 53 that is perpendicular to the longitudinal direction 51. Each pant 50 defines an assembled length 57 which extends in the longitudinal direction 51 from the waist end 56 to the crotch end 58. (If the front waistband portion 72 and the back waistband portion 74 are different distances from the crotch end 58, then the assembled length 57 of the pant is the longer of the two distances.) Each pant also defines a width 59 which extends in the transverse direction 53 from one side seam 55 to the other side seam 55. The length 57 and width 59 for purposes herein are measured when the pant is in a fully assembled (side seams intact), relaxed configuration, such as that depicted in FIG. 4. The length 57 is measured at the longitudinal centerline of the pant 50, and the width 59 is measured at the longitudinal midpoint of each side seam 55. Each pant further defines a first side portion 60, a second side portion 62, and a center portion 64 positioned transversely between the first side portion 60 and the second side portion 62. The first side portion 60 extends 20% to 40% of the transverse width 59 of the pant 50 in an assembled, laid-flat, relaxed configuration. The second side portion 62 extends 20% to 40% of the transverse width 59 of the pant 50 in an assembled, laid-flat, relaxed configuration. The center portion 64 extends approximately 20% to 50% of the width 59 of the pant 50 in an assembled, laid-flat, relaxed configuration. In particular embodiments, the first side portion 60, the second side portion 62, and the center portion 64 each extend approximately one-third of the width 59 of the pant 50 in a laid-flat, relaxed configuration, as is representatively illustrated in FIG. 4.

Figure 5:
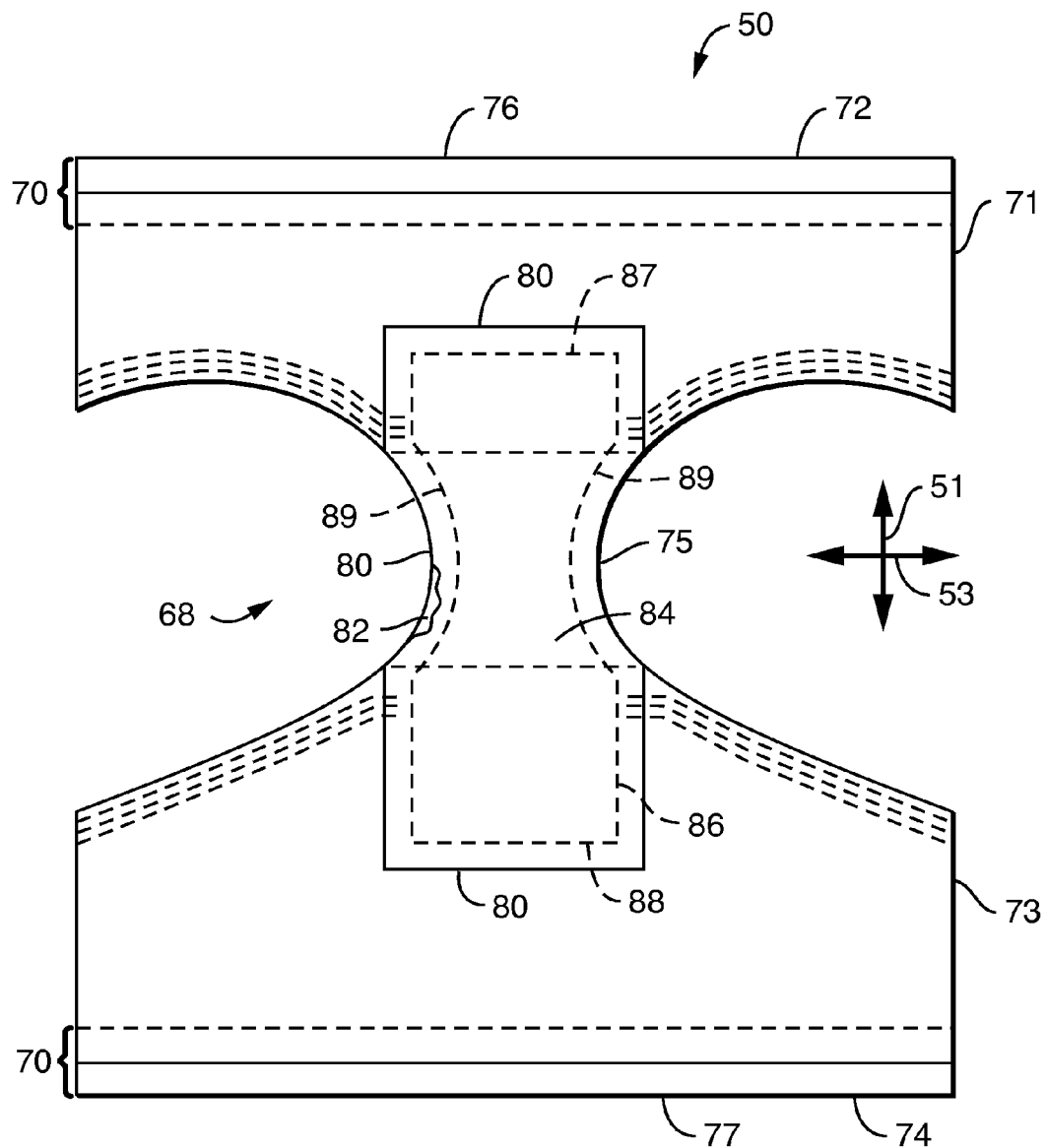
FIG. 5 representatively illustrates a top plan view of the disposable absorbent pant of FIG. 3 in a stretched and laid-flat configuration, prior to the joining of the front and back waist regions, and showing the surface of the article that faces the wearer when the article is worn.

Referring now to FIG. 5, the pant 50 of FIGS. 3 and 4 is illustrated in a longitudinally stretched and laid-flat configuration, prior to the joining of the front and back waist regions, and showing the surface of the article that faces the wearer when the article is worn. In this embodiment, the pant 50 includes a front panel 71, a back panel 73, and a crotch panel 75. The panels 71, 73, and 75 may be integral with each other, or may comprise separate components attached to one another. In particular embodiments, the front and back panels 71, 73 comprise elastomeric materials, such as elastomeric film laminates, elastomeric stranded laminates, elastomeric net or mesh laminates, or the like. In one example, the front and back panels 71, 73 each comprise an elastomeric film sandwiched between two polyolefin-based, cloth-like, nonwoven substrates.

Each pant 50 further defines a waistband region 70 which abuts the waist end 56 (FIG. 4). The waistband region 70 extends in the transverse direction 53 and at least partially encircles the waist opening 52 (FIG. 3). Each waistband region 70 comprises a front waistband portion 72 and a back waistband portion 74. Each waistband portion 72, 74 extends between the side seams 55 (FIG. 3). The front waistband portion 72 is adapted to contact the front half of a wearer's waist when donned, and the back waistband portion 74 is adapted to contact the back half of a wearer's waist when donned. The waistband portions 72, 74 can be integral with the front and back panels 71, 73, or can be separate components that are attached to the front and back panels 71, 73. For example, the front waistband portion 72 can constitute the region of the front panel 71 that is within 25 centimeters, or within 35 centimeters, of the front waist edge 76, and the back waistband portion 74 can constitute the region of the back panel 73 that is within 25 centimeters, or within 35 centimeters, of the back waist edge 77. Alternatively, the front waistband portion 72 can comprise a folded-over portion of the front panel 71, and/or the back waistband portion 74 can comprise a folded-over portion of the back panel 73. In particular embodiments, a transversely extending fold line defines the front waist edge 76, and a transversely extending fold line defines the back waist edge 77. In such embodiments, the longitudinal length of the folded portion defines the boundaries of the respective waistband portion. Desirably, one or more elastic strands are disposed within one or both folded-over portions. Examples of such folded-over waistband configurations are shown in U.S. Patent Application Publication 2008/0134487 to Hartono, which is incorporated by reference to the extent consistent herewith. Alternatively, the front waistband portion 72 can comprise a separate elastomeric component or assembly affixed to the front panel 71, and/or the back waistband portion 74 can comprise a separate elastomeric component or assembly affixed to the back panel 73, as representatively illustrated in FIG. 5.

Each pant also desirably includes an absorbent composite 80 generally disposed in the center portion 64 and in the crotch region 68. In particular embodiments, the absorbent composite 80 can, but need not, include a liquid-impermeable garment-side backsheet 82, a liquid-permeable body-side topsheet 84, and a fluid-absorbing core 86 comprised of fluff pulp and/or superabsorbent polymer sandwiched between the backsheet 82 and the topsheet 84. The absorbent core 86 has a front edge 87, a back edge 88 spaced from the front edge in the longitudinal direction, and two side edges 89 which extend from the front edge 87 to the back edge 89. The absorbent core 86 may be rectangular, hour-glass, oval, trapezoid, or other suitable shape. Due to the additional bulk introduced by an absorbent core 86, the crotch region 68 of a pant 50 that includes an absorbent core 86 is generally thicker than the waistband region 70 of such pant. Examples of disposable absorbent pants having certain aspects suitable for incorporation into particular embodiments of the present invention include those disclosed in U.S. Pat. No. 5,745,922 issued May 5, 1998 to Rajala et al., U.S. Pat. No. 6,240,569 issued Jun. 5, 2001 to Van Gompel et al., U.S. Pat. No. 6,702,798 issued Mar. 9, 2004 to Christoffel et al., and U.S. Pat. No. 7,604,624 issued Oct. 20, 2009 to Veith et al., the contents of each is hereby incorporated by reference to the extent consistent herewith. Note that the disposable absorbent pants could be provided in a permanently "closed" (i.e., pull-on style) configuration, a releasably and refastenably "closed" configuration, or an "open" (i.e., non-prefastened) configuration—any of which could be used in conjunction with the various embodiments of the present invention.

In various embodiments, the pants of the present invention may be disposed within the housing portion in any suitable folded configuration. In some embodiments, a package of folded pants may have a first pant with a first folded configuration and a second pant with a second folded configuration. The first folded configuration may be the same as the second folded configuration or may be different than the second folded configuration.

Figure 6A:
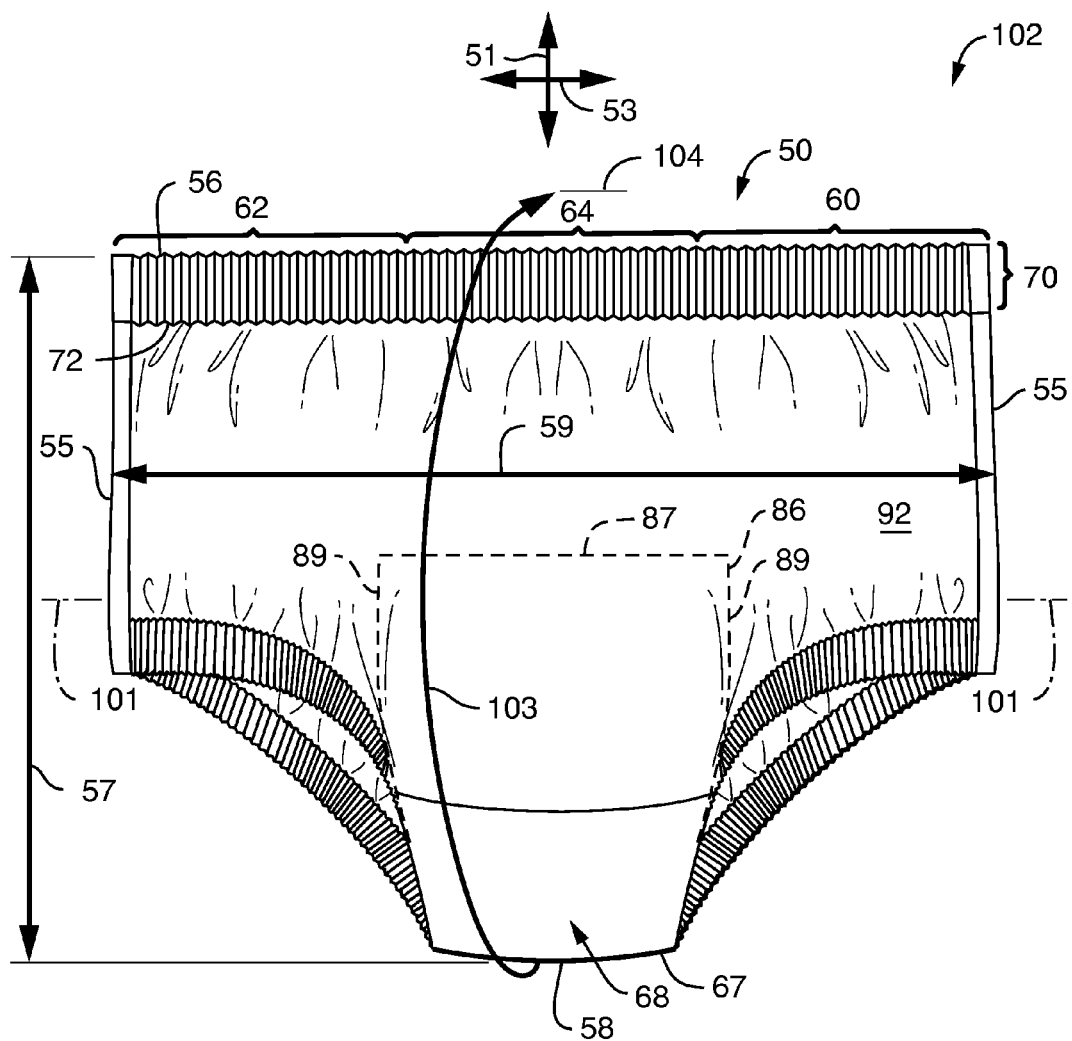
FIG. 6A representatively illustrates a front plan view of the disposable absorbent pant of FIG. 3 in a pre-folded configuration.
Figure 6B:
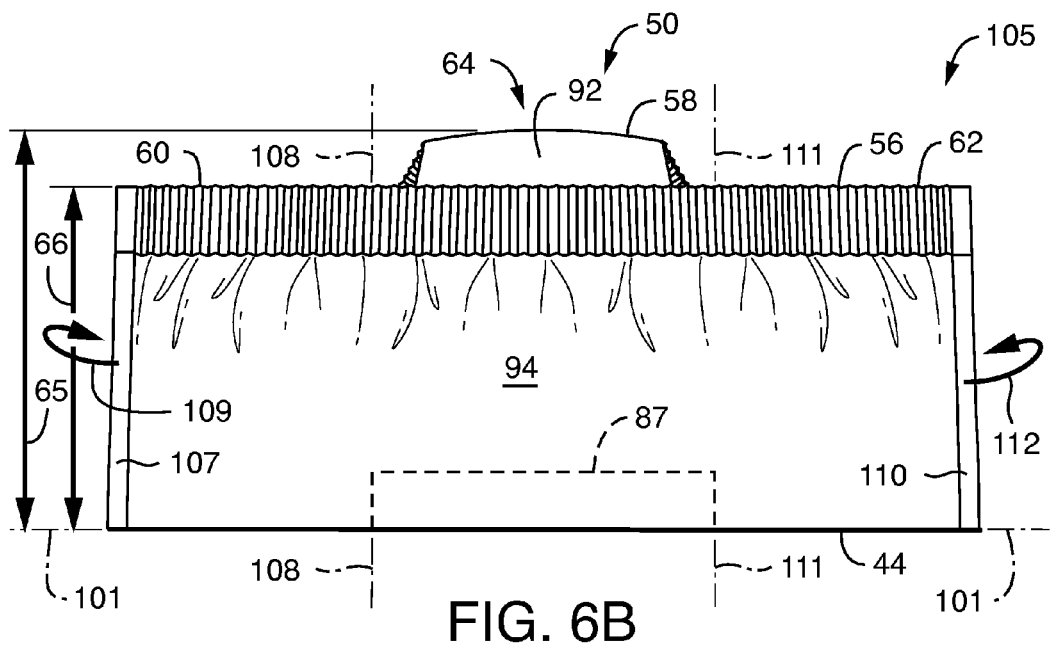
FIG. 6B representatively illustrates a plan view of a first side of the disposable absorbent pant of FIG. 3 in a first folded configuration.
Figure 6C:
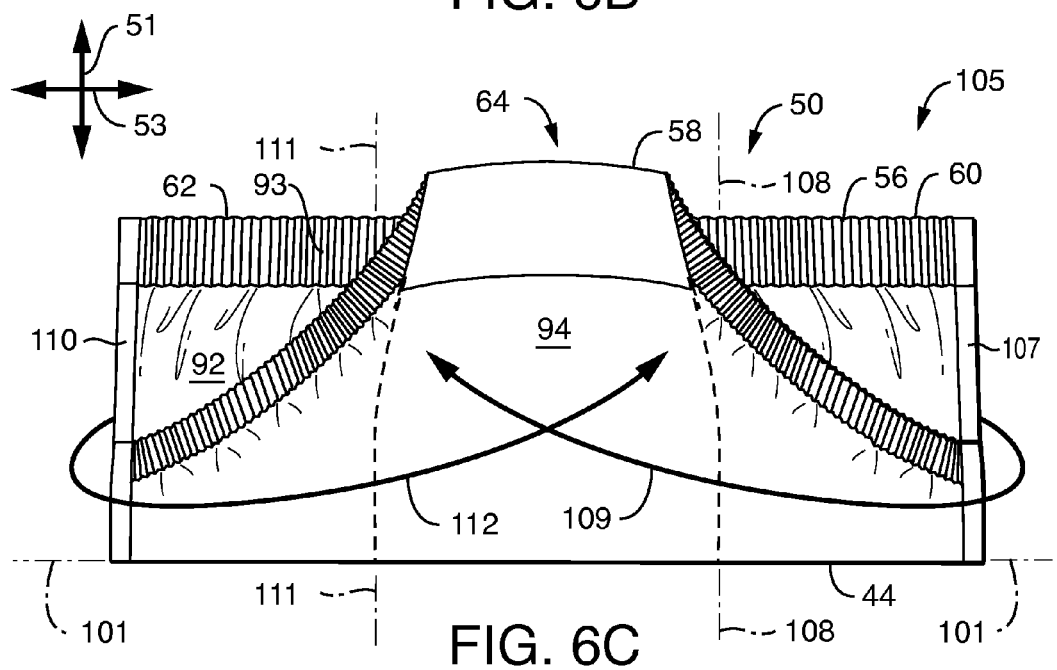
FIG. 6C representatively illustrates a plan view of a second side, opposite the first side, of the pant of FIG. 3 in the first folded configuration.
Figure 6D:
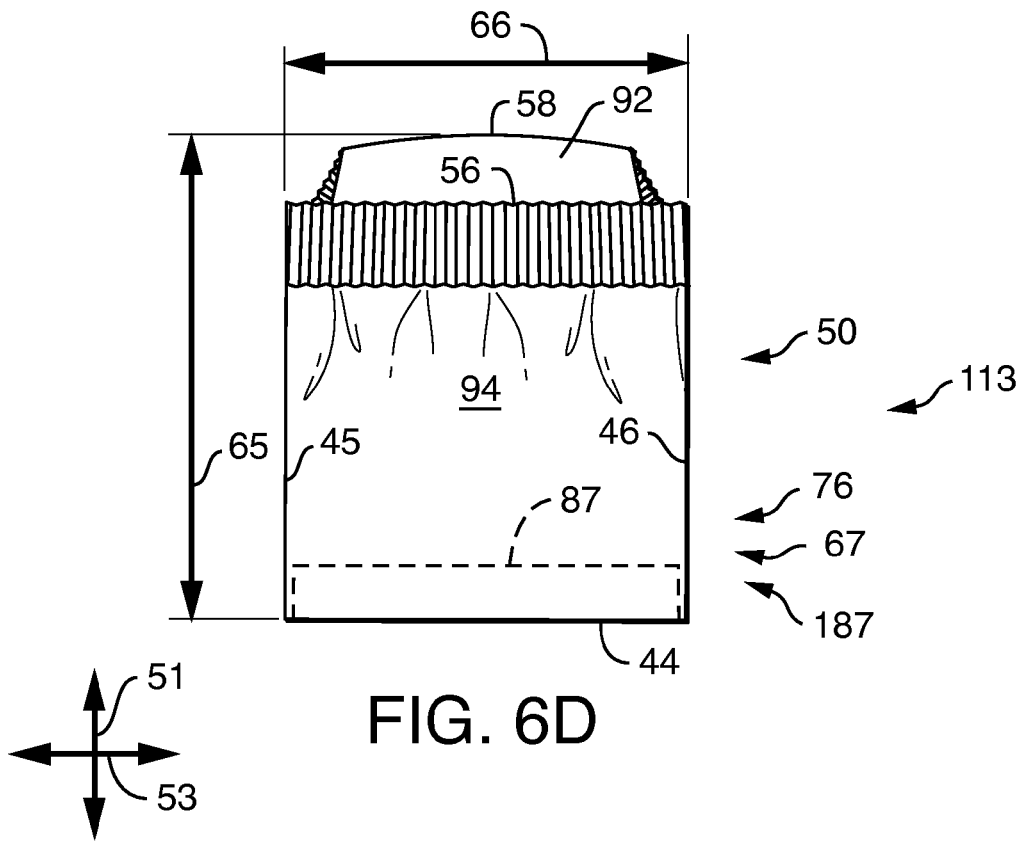
FIG. 6D representatively illustrates a plan view of a first side of the disposable absorbent pant of FIG. 3 in a second folded configuration.
Figure 6E:
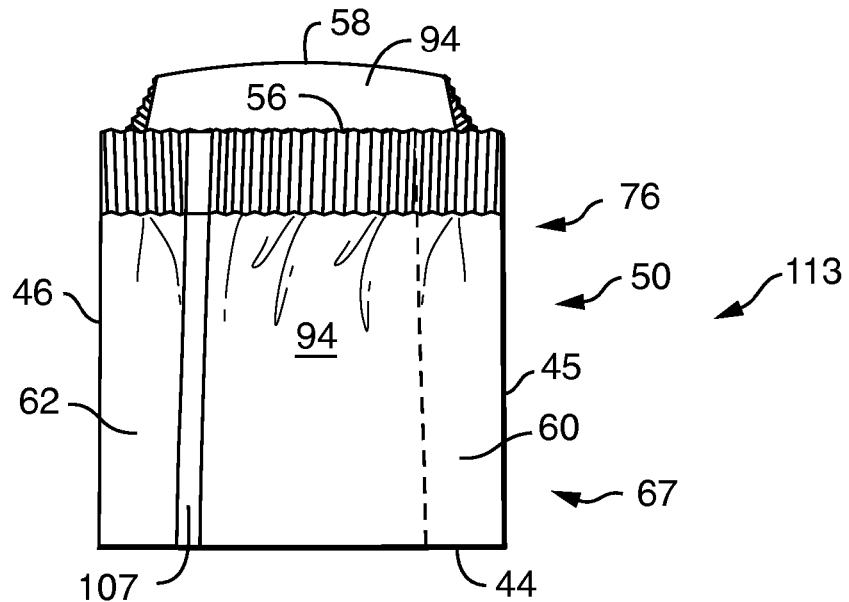
FIG. 6E representatively illustrates a plan view of a second side, opposite the first side, of the pant of FIG. 3 in the second folded configuration.

Referring now to FIGS. 6A, 6B, 6C, 6D, and 6E, an exemplary pant 50 is illustrated in various pre-folded and folded configurations. In FIG. 6A, the pant 50 is illustrated in a pre-folded configuration 102 with the front side 92 of the pant 50 facing the viewer in a first view and the back side 94 of the pant facing away from the viewer in a second view opposite the first view. As used herein, the term "front side" refers to the side of the pant designed to be worn towards the wearer's front and the term "back side" refers to the side of the pant designed to be worn towards the wearer's back. The crotch end 58 is folded along line 101 in the direction indicated by arrow 103 to a position 104 beyond the waist end 56 to define a first folded edge 44 and a first folded configuration 105 as illustrated in FIGS. 6B and 6C. FIG. 6B illustrates the second view of the pant 50 in the first folded configuration 105. FIG. 6C illustrates the first view of the pant 50 in the first folded configuration 105. A first side edge 107 and a first side portion 60 are folded along a line 108 in the direction indicated by the arrow 109 to define a second folded edge 45. Likewise, a second side portion 62 and a second side edge 110 are folded along a line 111 in the direction indicated by the arrow 112 to define a third folded edge 46. The pant 50 is now in a second folded configuration 113 as illustrated in FIGS. 6D and 6E. FIG. 6D illustrates the second view of the pant 50 in the second folded configuration 113. FIG. 6E illustrates the first view of the pant 50 in the second folded configuration 113. The side 60 is overlaid on the side 62 in FIG. 6E but in some embodiments, the side 62 may be overlaid on the side 60 (not illustrated). In some embodiments, the first side portion and/or the second side portion may be directly folded over on the center portion. In other embodiments, the first side portion and/or the second side portion may be z-folded to create one or more pleats and to accommodate longer side portions.

Figure 7A:
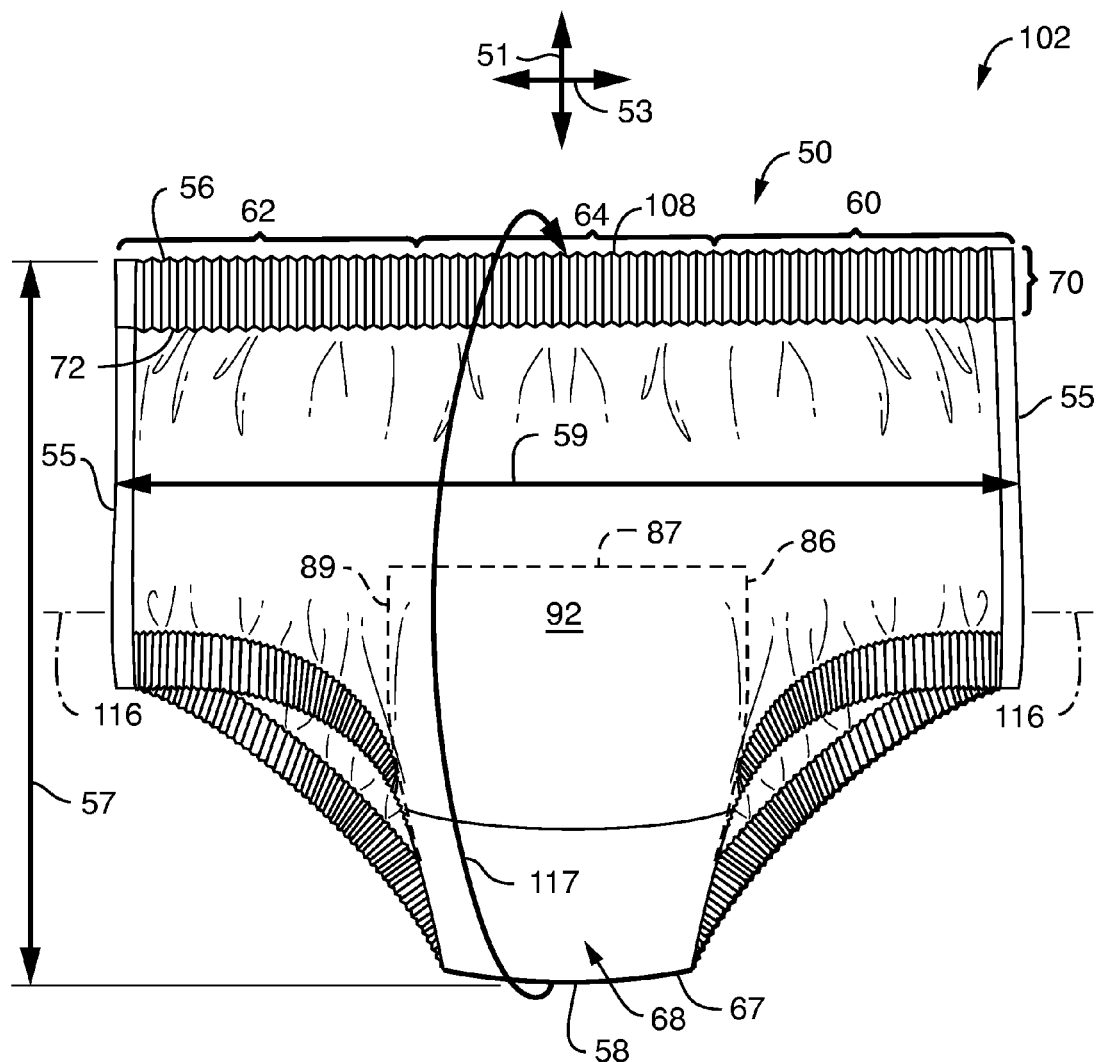
FIG. 7A representatively illustrates a front plan view of the disposable absorbent pant of FIG. 3 in a pre-folded configuration.
Figure 7B:
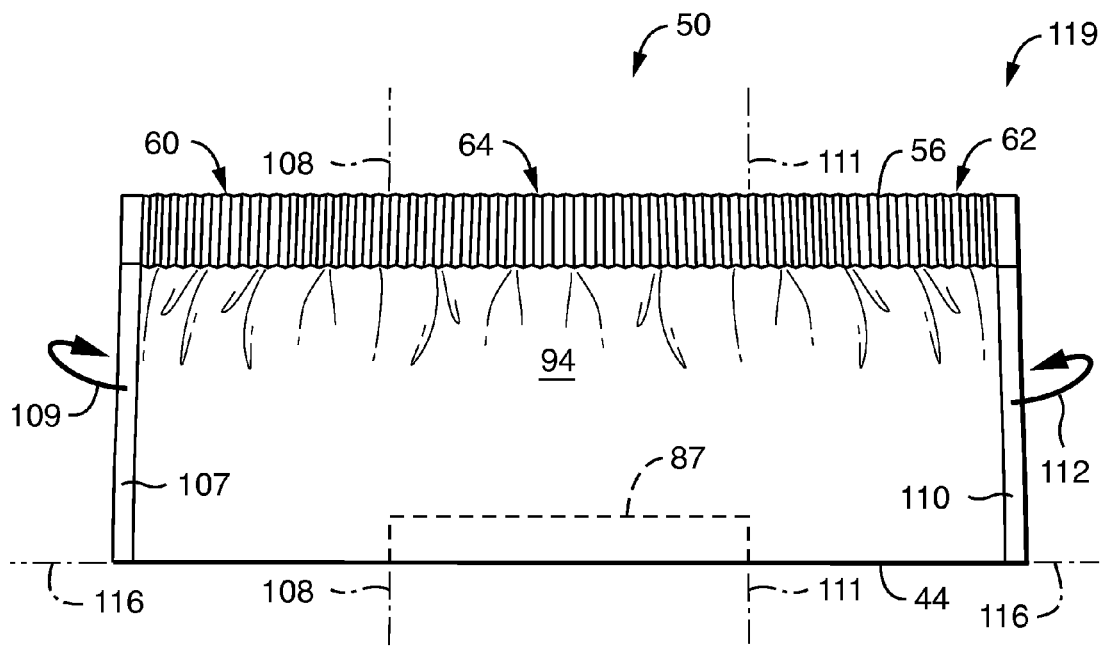
FIG. 7B representatively illustrates a plan view of a first side of the disposable absorbent pant of FIG. 3 in a third folded configuration.
Figure 7C:
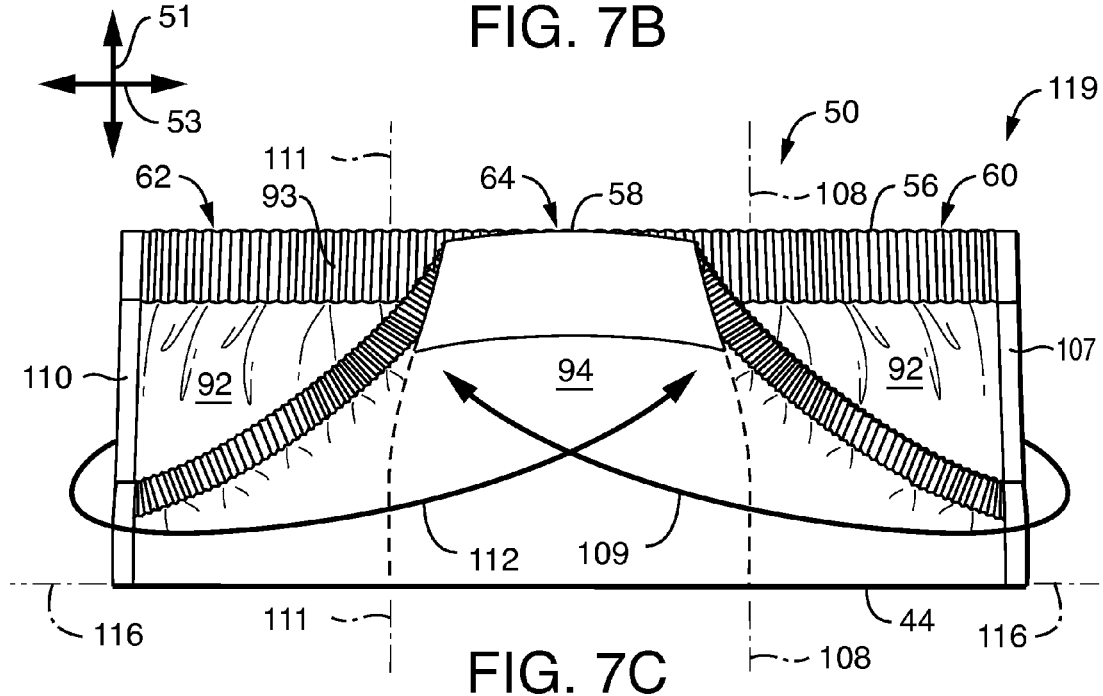
FIG. 7C representatively illustrates a plan view of a second side, opposite the first side, of the pant of FIG. 3 in the third folded configuration.
Figure 7D:
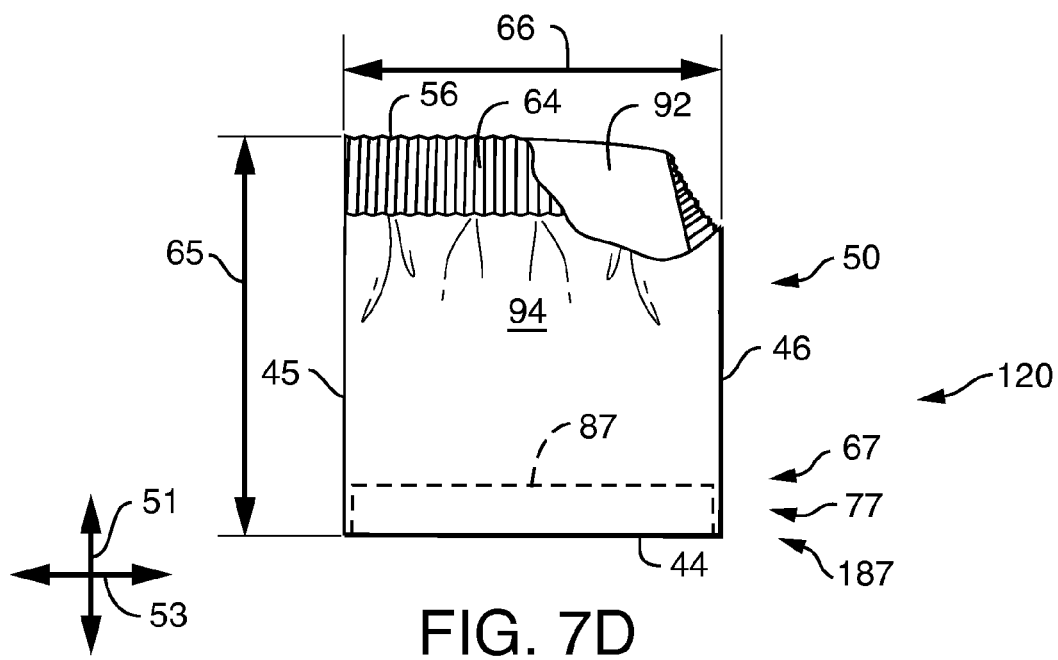
FIG. 7D representatively illustrates a plan view of a first side of the disposable absorbent pant of FIG. 3 in a fourth folded configuration.
Figure 7E:
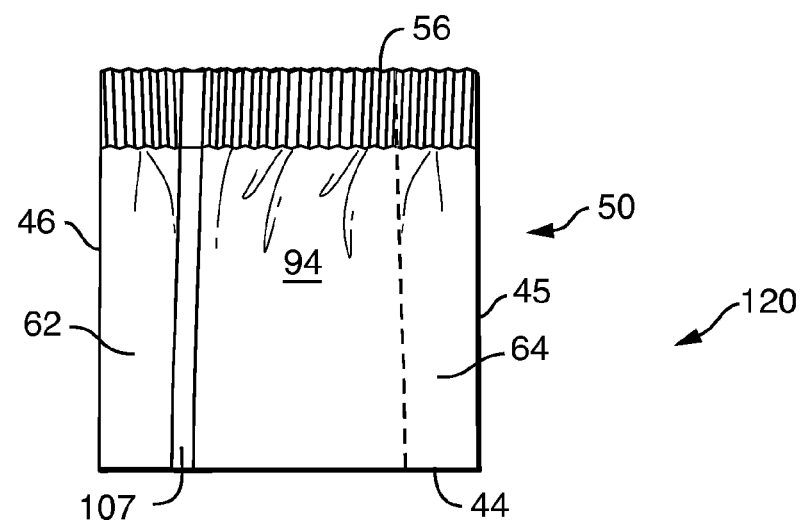
FIG. 7E representatively illustrates a plan view of a second side, opposite the first side, of the pant of FIG. 3 in the fourth folded configuration.

Referring now to FIGS. 7A, 7B, 7C, 7D, and 7E, an exemplary pant 50 is illustrated in various pre-folded and folded configurations. In FIG. 7A, the pant 50 is illustrated in a pre-folded configuration 102 with the front side 92 of the pant 50 facing the viewer in a first view and the back side 94 of the pant facing away from the viewer in a second view opposite the first view. In this embodiment, the crotch end 58 is folded along line 116 in the direction indicated by arrow 117 to a position 108 that is at or near the waist end 56 to define a first folded edge 44 and a third folded configuration 119 as illustrated in FIGS. 7B and 7C. FIG. 7B illustrates the second view of the resultant pant 50 in the third folded configuration 119. FIG. 7C illustrates the first view of the resultant pant 50 in the third folded configuration 119. A first side edge 107 and a first side portion 60 are folded along a line 108 in the direction indicated by the arrow 109 to overlay the center portion 64 and define a second folded edge 45. Likewise, a second side edge 110 and the second side portion 62 are folded along a line 111 in the direction indicated by the arrow 112 to overlay the center portion 64 and define a third folded edge 46. The pant 50 is now in a fourth folded configuration 120 as illustrated in FIGS. 7D and 7E. FIG. 7D illustrates the second view of the resultant pant 50 in the fourth folded configuration 120 with a portion cut away to illustrate underlying detail. FIG. 7E illustrates the first view of the resultant pant 50 in the fourth folded configuration 120. FIG. 7E also illustrates the first side portion 60 overlaying the second side portion 62 which in turn overlays the center portion 64 (FIG. 7D). In other embodiments, the second side portion may overlay the first side portion which may overlay the center portion. In some embodiments, the first side portion and/or the second side portion may be directly folded over on the center portion. In other embodiments, the first side portion and/or the second side portion may be z-folded to create one or more pleats and to accommodate longer side portions.

Figure 8A:
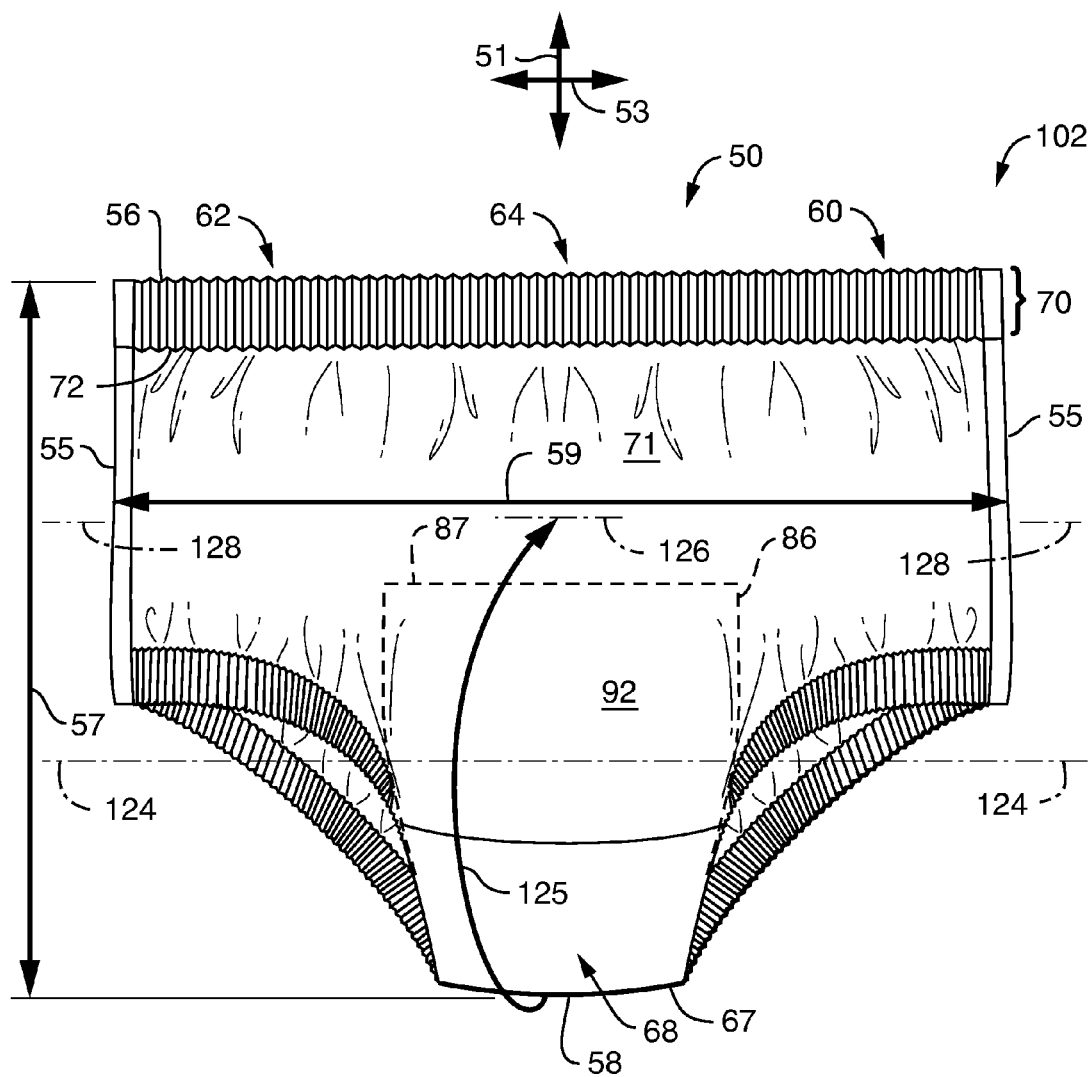
FIG. 8A representatively illustrates a front plan view of the disposable absorbent pant of FIG. 3 in a pre-folded configuration.
Figure 8B:
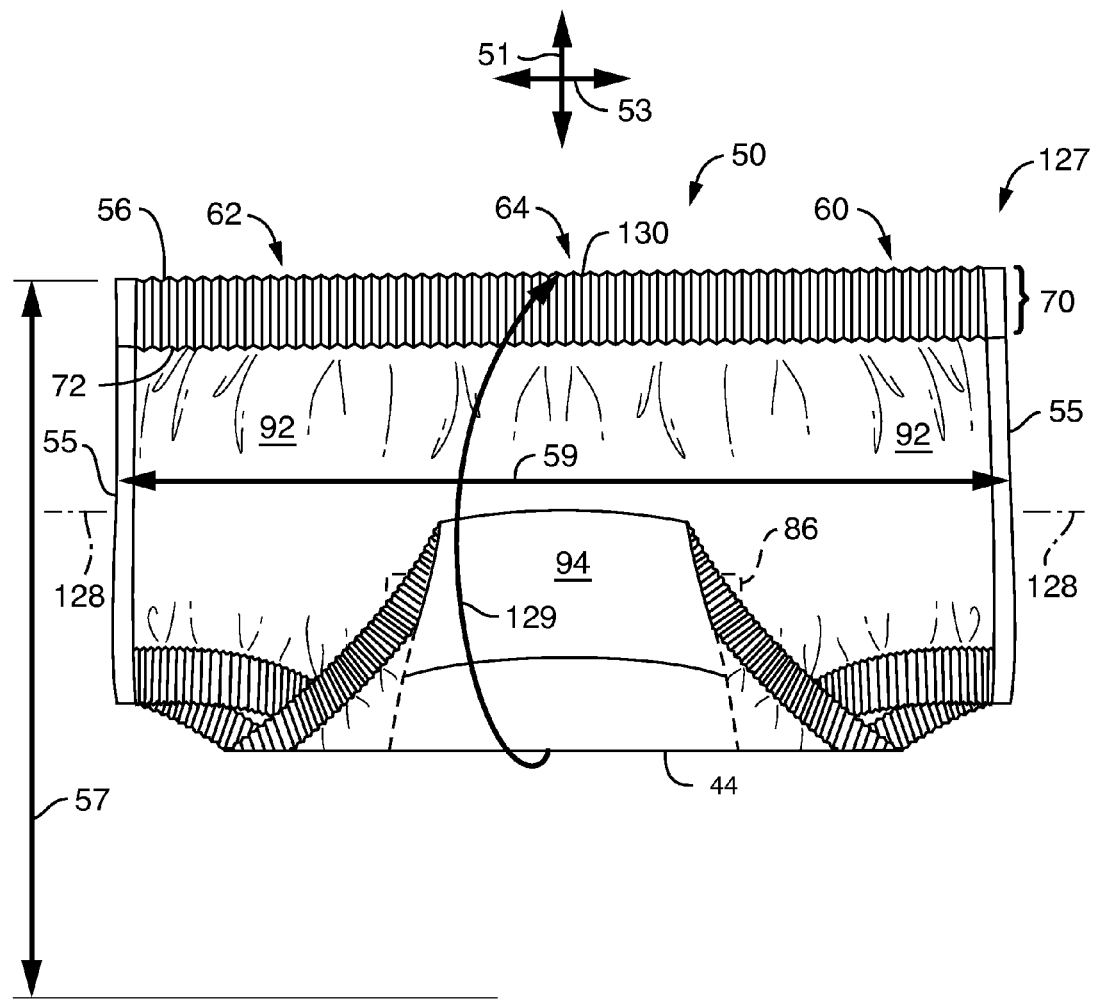
FIG. 8B representatively illustrates a plan view of the disposable absorbent pant of FIG. 3 in a fifth folded configuration.
Figure 8C:
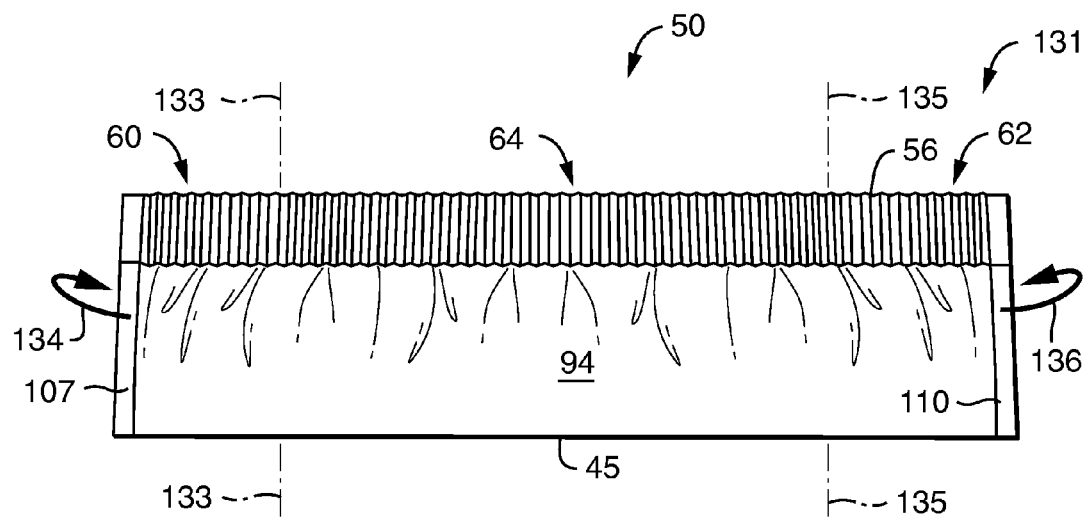
FIG. 8C representatively illustrates a plan view of a first side of the disposable absorbent pant of FIG. 3 in a sixth folded configuration.
Figure 8D:
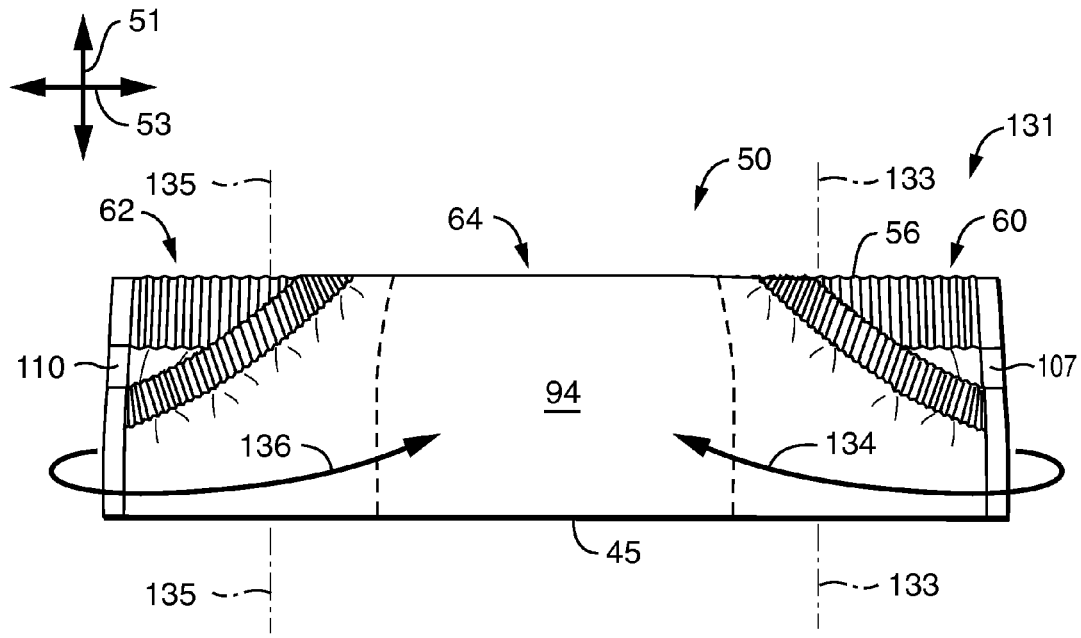
FIG. 8D representatively illustrates a plan view of a second side, opposite the first side, of the pant of FIG. 3 in the sixth folded configuration.

Referring now to FIGS. 8A-8J, an exemplary pant 50 is illustrated in various pre-folded and folded configurations. In FIG. 8A, the pant 50 is illustrated in a pre-folded configuration 102 with the front side 92 of the pant 50 facing the viewer in a first view and the back side 94 of the pant facing away from the viewer in a second view opposite the first view. In this embodiment, the crotch end 58 is folded along line 124 in the direction indicated by arrow 125 to a position 126 in the front waist panel 71 to define a first folded edge 44 and a fifth folded configuration 127 as illustrated in FIG. 8B. FIG. 8B illustrates the first view of the resultant pant 50 in the fifth folded configuration 127. The folded edge 44 is folded along line 128 in the direction indicated by arrow 129 to a position 130 that is at or near the waist end 56 to define a second folded edge 45 and a sixth folded configuration 131 as illustrated in FIGS. 8C and 8D.

Figure 8E:
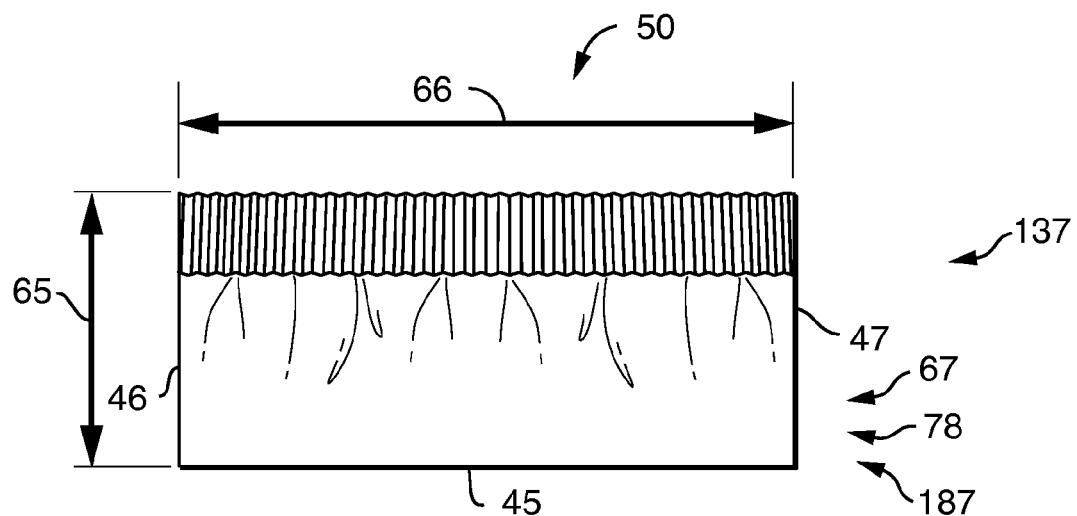
FIG. 8E representatively illustrates a plan view of a first side of the disposable absorbent pant of FIG. 3 in a seventh folded configuration.
Figure 8F:
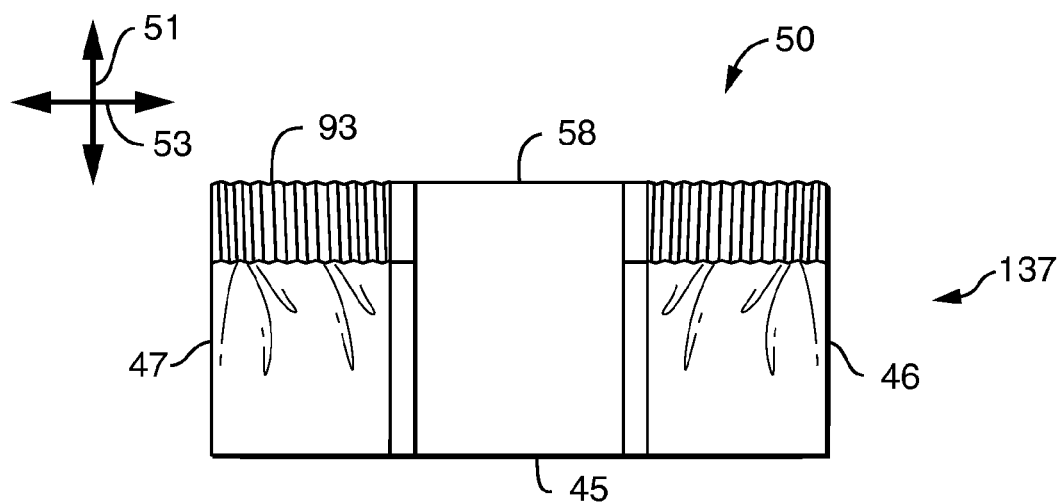
FIG. 8F representatively illustrates a plan view of a second side, opposite the first side, of the pant of FIG. 3 in the seventh folded configuration.

In one embodiment, starting with the sixth folded configuration 131 as illustrated in FIGS. 8C and 8D, a first side edge 107 and first side portion 60 are folded along a line 133 in the direction indicated by the arrow 134 to overlay center portion 64 and define a third folded edge 46. Likewise, a second side edge 110 and the second side portion 62 are folded along a line 135 in the direction indicated by the arrow 136 to overlay the center portion 64 and define a fourth fold edge 47. The pant 50 is now in a seventh folded configuration 137 as illustrated in FIGS. 8E and 8F. FIG. 8E illustrates the second view of the resultant pant 50 in the seventh folded configuration 137. FIG. 8F illustrates the first view of the resultant pant 50 in the seventh folded configuration 137. In some embodiments, the first side portion and/or the second side portion may be directly folded over on the center portion. In other embodiments, the first side portion and/or the second side portion may be z-folded to create one or more pleats and to accommodate longer side portions.

Figure 8G:
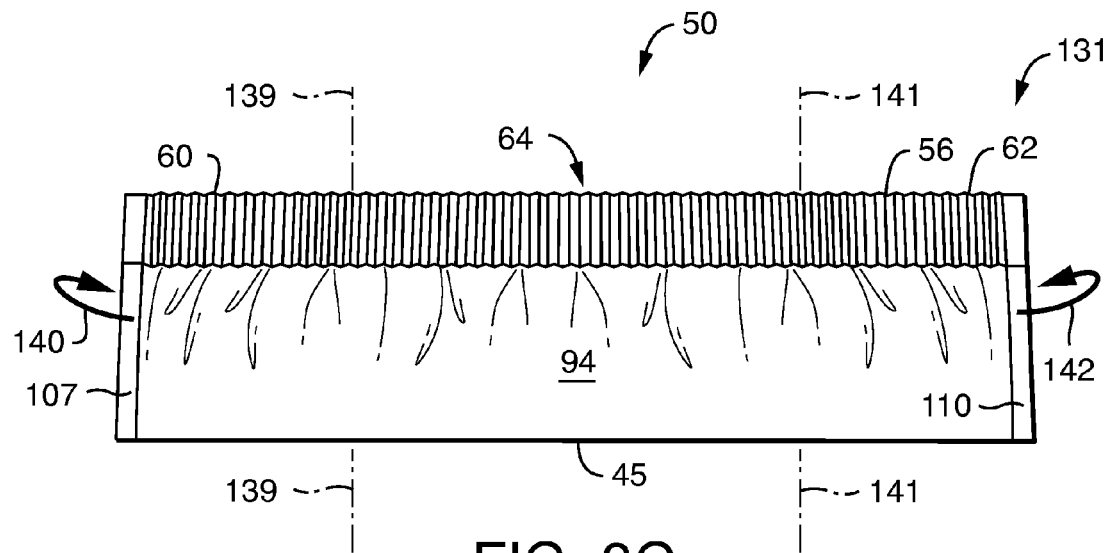
FIG. 8G representatively illustrates a plan view of a first side of the disposable absorbent pant of FIG. 3 in the sixth folded configuration.
Figure 8H:
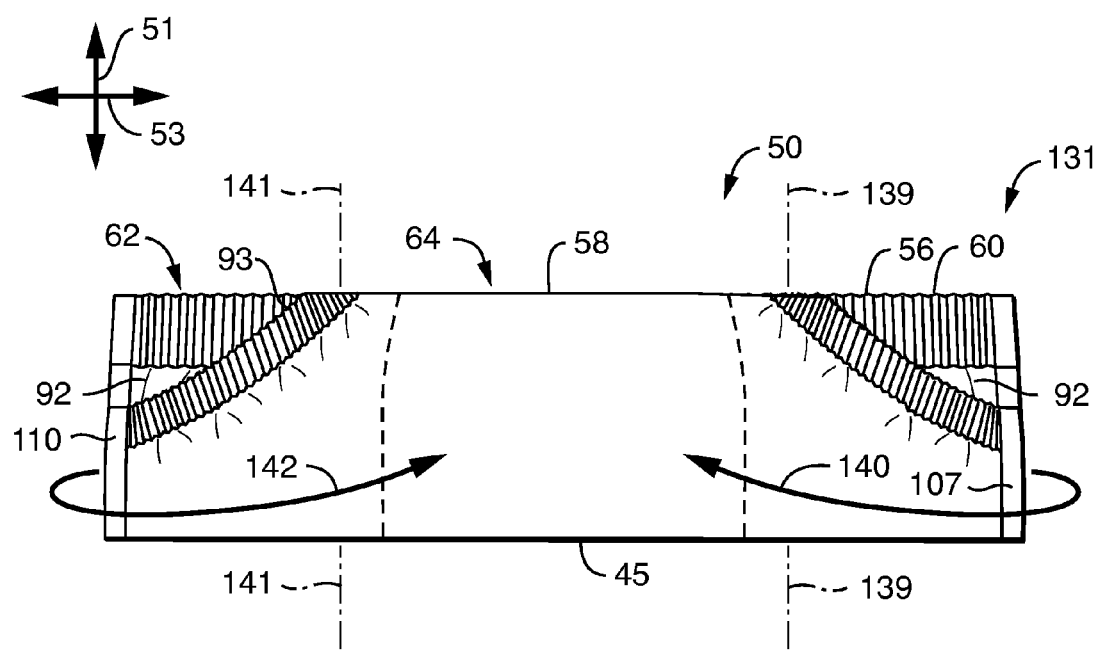
FIG. 8H representatively illustrates a plan view of a second side, opposite the first side, of the pant of FIG. 3 in the sixth folded configuration.
Figure 8I:
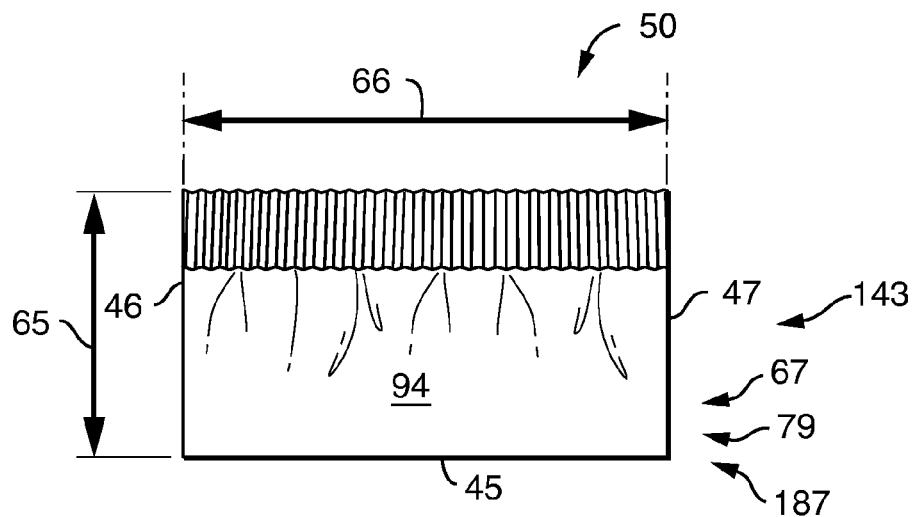
FIG. 8I representatively illustrates a plan view of a first side of the disposable absorbent pant of FIG. 3 in an eighth folded configuration.
Figure 8J:
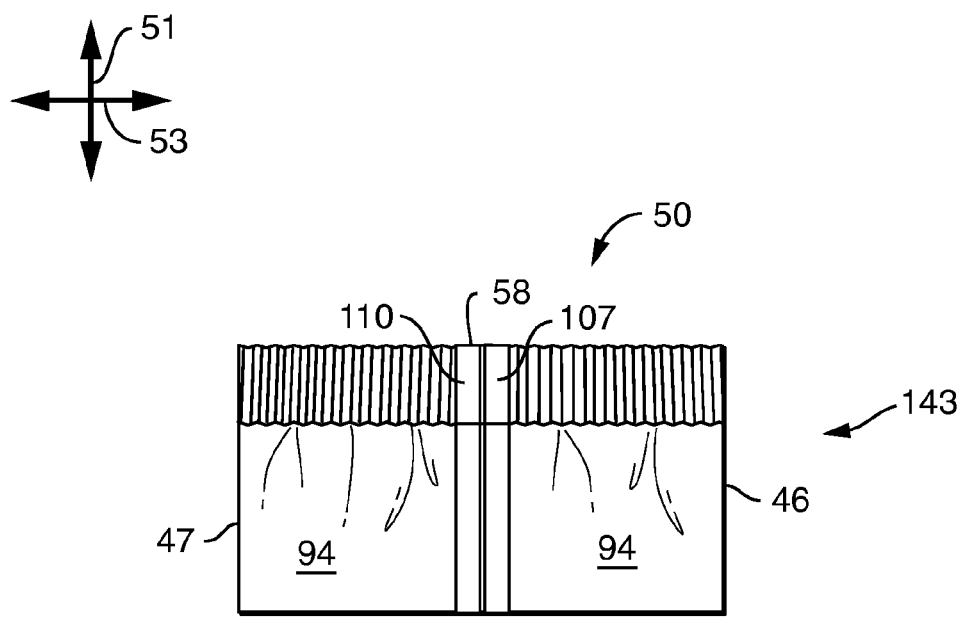
FIG. 8J representatively illustrates a plan view of a second side, opposite the first side, of the pant of FIG. 3 in the eighth folded configuration.

In another embodiment, starting with the sixth folded configuration 131 as illustrated in FIGS. 8G and 8H, a first side edge 107 and first side portion 60 are folded along a line 139 in the direction indicated by the arrow 140 to overlay the center portion 64 and define a third folded edge 46. Likewise, a second side edge 110 and the second side portion 62 are folded along a line 141 in the direction indicated by the arrow 142 to overlay the center portion 64 and define a fourth fold edge 47. The pant 50 is now in an eighth folded configuration 143 as illustrated in FIGS. 8I and 8J. FIG. 8I illustrates the second view of the resultant pant 50 in the eighth folded configuration 143. FIG. 8J illustrates the first view of the resultant pant 50 in the eighth folded configuration 143. In some embodiments, the first side portion and/or the second side portion may be directly folded over on the center portion. In other embodiments, the first side portion and/or the second side portion may be z-folded to create one or more pleats and to accommodate longer side portions.

Figure 9A:
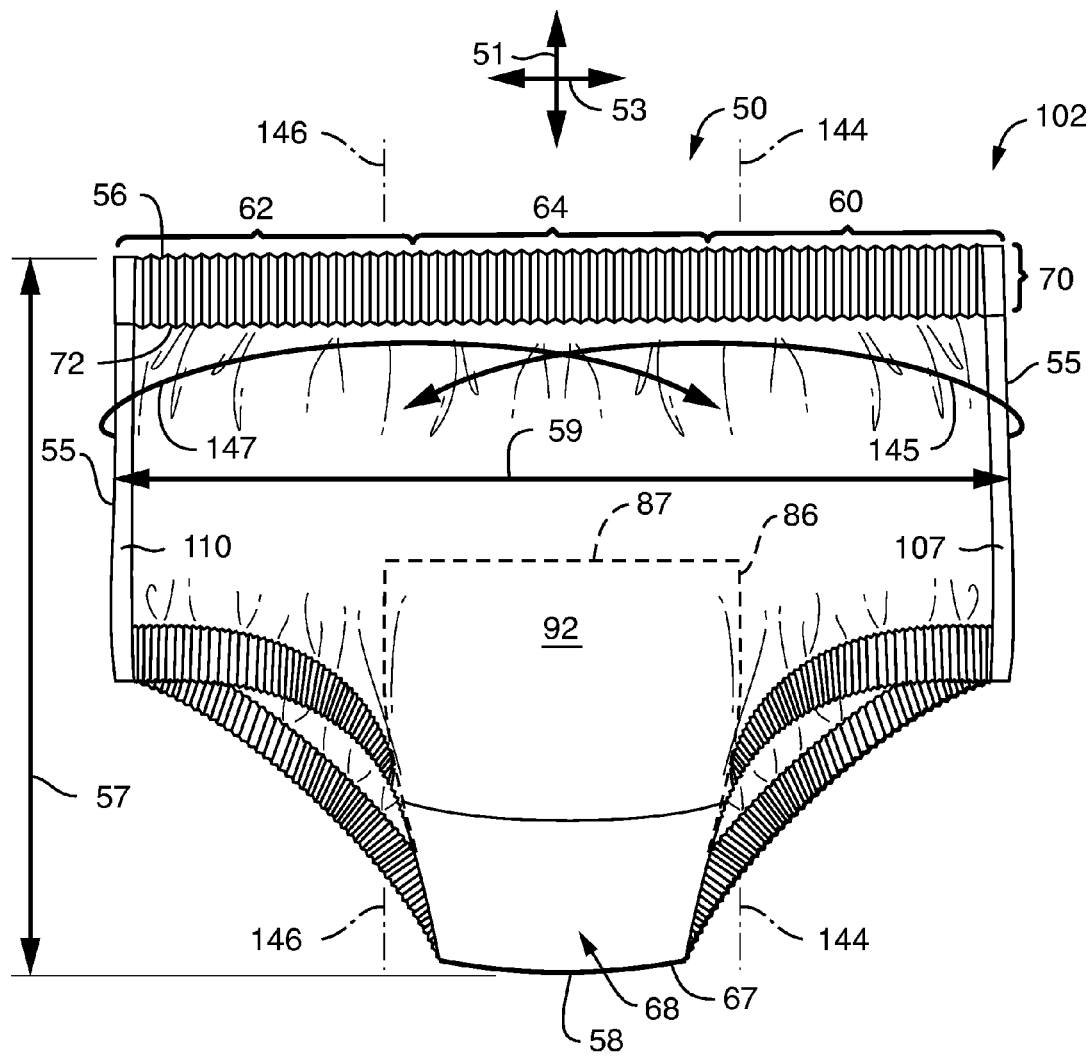
FIG. 9A representatively illustrates a front plan view of the disposable absorbent pant of FIG. 3 in a pre-folded configuration.
Figure 9B:
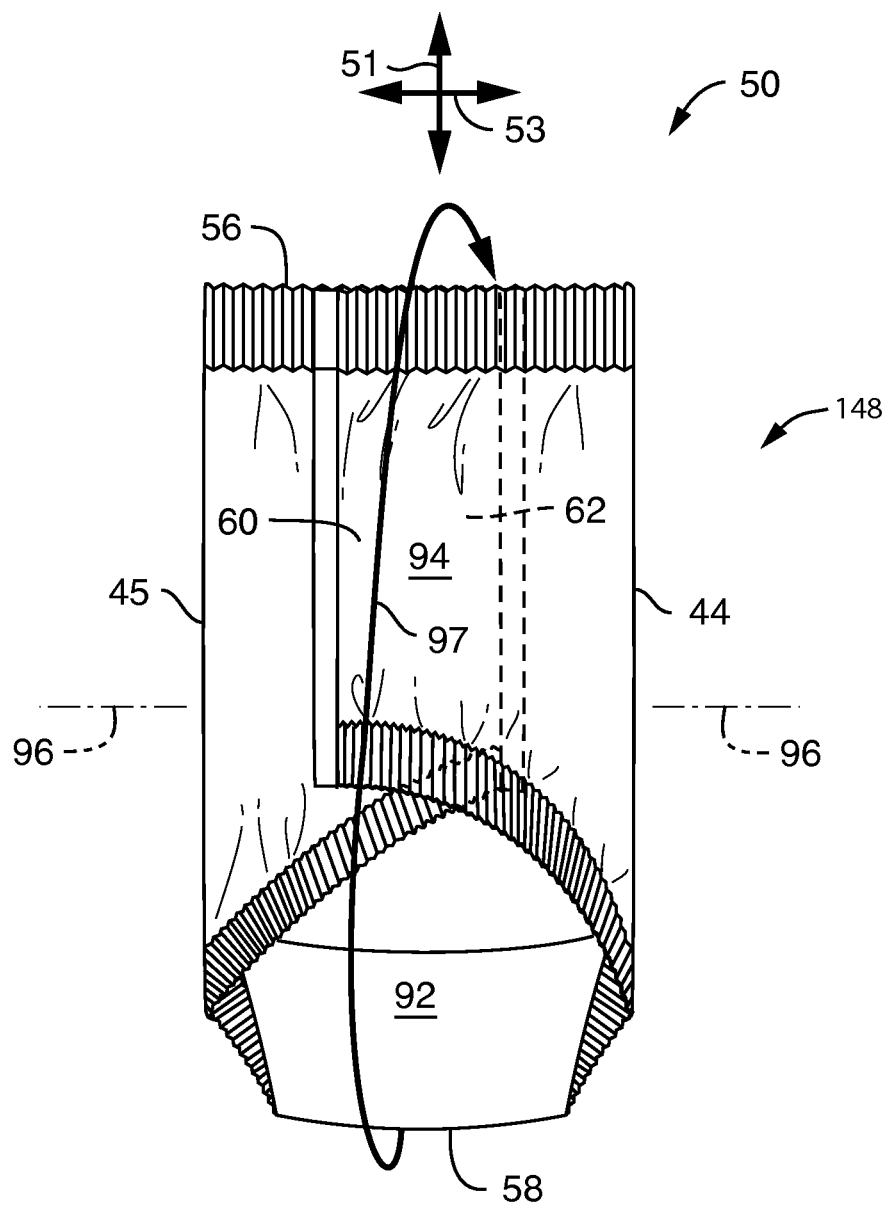
FIG. 9B representatively illustrates a plan view of the disposable absorbent pant of FIG. 3 in a ninth folded configuration.
Figure 9C:
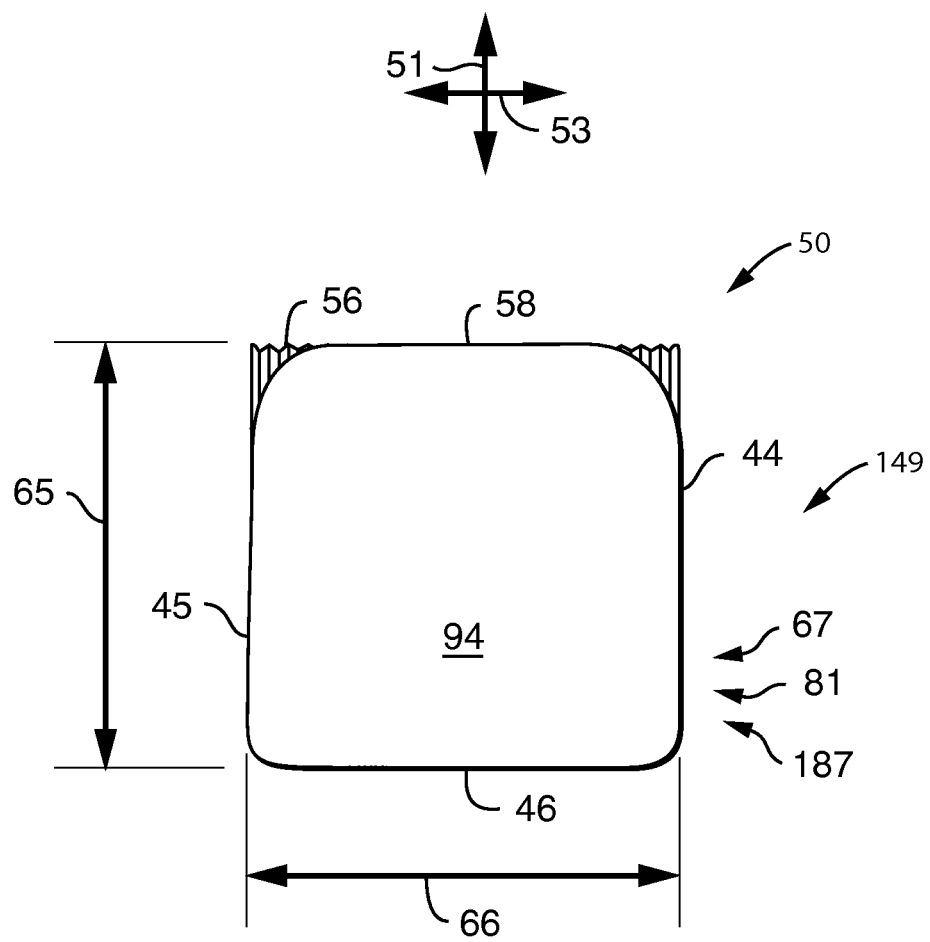
FIG. 9C representatively illustrates a plan view of a first side of the disposable absorbent pant of FIG. 3 in a tenth folded configuration.

Referring now to FIGS. 9A, 9B, and 9C, an exemplary pant 50 is illustrated in various pre-folded and folded configurations. In FIG. 9A, the pant 50 is illustrated in a pre-folded configuration 102 with the front side 92 of the pant 50 facing the viewer in a first view and the back side 94 of the pant facing away from the viewer in a second view opposite the first view. A first side edge 107 and a first side portion 60 are folded along a line 144 in the direction indicated by the arrow 145 to define a first folded edge 44. Likewise, a second side portion 62 and a second side edge 110 are folded along a line 146 in the direction indicated by the arrow 147 to define a second folded edge 45. The pant 50 is now in a first folded configuration 148 as illustrated in FIG. 9B. In some embodiments, the first side portion and/or the second side portion may be directly folded over on the center portion. In other embodiments, the first side portion and/or the second side portion may be z-folded to create one or more pleats and to accommodate longer side portions.

The crotch end 58 is folded along line 96 in the direction indicated by arrow 97 to a position proximate the waist end 56 to define a third folded edge 46 and a second folded configuration 149 as illustrated in FIG. 9C. The side 60 is overlaid on the side 62 in FIG. 9B but in some embodiments, the side 62 may be overlaid on the side 60 (not illustrated).

In the various folded configurations, the pant 50 defines a folded pant length 65, a folded pant width 66, and a folded pant area 67. The folded pant length 65 is the maximum dimension of the folded pant 50 as measured in the longitudinal direction 51. The folded pant width 66 is the maximum dimension of the folded pant 50 as measured in the transverse direction 53. The folded pant area 76 is the total surface area of the pant in the plane defined by the longitudinal direction 51 and the transverse direction 53.

In various embodiments, the pants may have any suitable folded length. In some embodiments, the folded pant length 65 may be 5 inches (127 mm) to 8.5 inches (216 mm). In some embodiments, the folded pant length 65 in the second folded configuration 113 may be 6 inches (152 mm) to 6.5 inches (165 mm). In some embodiments, the folded pant length 65 in the fourth folded configuration 120 may be 5 inches (127 mm) to 5.5 inches (140 mm). In some embodiments, the folded pant length 65 in the seventh folded configuration 137 may be 5 inches (127 mm) to 5.5 inches (140 mm). In some embodiments, the folded pant length 65 in the eighth folded configuration 143 may be 5.5 inches (140 mm) to 6 inches (152 mm). In some embodiments, the folded pant length 65 in the tenth folded configuration 149 may be 8 inches (203 mm) to 8.5 inches (216 mm).

In various embodiments, the pants may have any suitable folded width. In some embodiments, the folded pant width 66 may be 4.75 inches (121 mm) to 8 inches (203 mm). In some embodiments, the folded pant width 66 in the second folded configuration 113 may be 4.5 inches (114 mm) to 5.5 inches (140 mm) or about 5 inches (127 mm). In some embodiments, the folded pant width 66 in the fourth folded configuration 120 may be 4.75 inches (121 mm) to 5.5 inches (140 mm) or about 5 inches (127 mm). In some embodiments, the folded pant width 66 in the seventh folded configuration 137 may be 6.75 inches (171 mm) to 8 inches (203 mm). In some embodiments, the folded pant width 66 in the eighth folded configuration 143 may be 4.75 inches (121 mm) to 6 inches (152 mm). In some embodiments, the folded pant width 66 in the tenth folded configuration 149 may be 4.75 inches (121 mm) to 5.5 inches (140 mm).

In various embodiments, the pants may have any suitable folded area. For example, the pant 50 illustrated in FIG. 6D is in the second folded configuration 113 and defines a first folded area 76. The pant 50 illustrated in FIG. 7D is in the fourth folded configuration 120 and defines a second folded area 77. The pant 50 illustrated in FIG. 8E is in the seventh folded configuration 137 and defines a third folded area 78. The pant 50 illustrated in FIG. 8I is in the eighth folded configuration 143 and defines a fourth folded area 79. The pant 50 illustrated in FIG. 9C is in the tenth folded configuration 149 and defines a fifth folded area 81.

In various embodiments, the folded pant area 67 may be 17200 mm² to 28600 mm². In some embodiments, the first folded pant area 76 in the second folded configuration 113 may be 17200 mm² to 22400 mm² as illustrated in FIG. 6D. In some embodiments, the second folded pant area 77 in the fourth folded configuration 120 may be 18200 mm² to 23400 mm² as illustrated in FIG. 7D. In some embodiments, the third folded pant area 78 in the seventh folded configuration 137 may be 19500 mm² to 24500 mm² as illustrated in FIG. 8E. In some embodiments, the fourth folded pant area 79 in the eighth folded configuration 143 may be 18200 mm² to 23400 mm² as illustrated in FIG. 8I. In some embodiments, the fifth folded pant area 81 in the tenth folded configuration 149 may be 26000 mm² to 28600 mm² as illustrated in FIG. 9C.

In various embodiments a package may include a first folded pant having a first folded pant area, a second folded pant having a second folded pant area, a third folded pant having a third folded pant area, and/or a fourth pant having a fourth folded pant area. In various embodiments, the first folded pant area 76, the second folded pant area 77, the third folded pant area 78, and/or the fourth folded pant area 79 may be the same or may be different or may have a combination of areas. For example, in some embodiments, the first folded area 76, as illustrated in FIG. 6D, may be greater than the second folded area 77 as illustrated in FIG. 7D. In some embodiments, the third folded area 78, as illustrated in FIG. 8E, may be greater than the fourth folded area 79, as illustrated in FIG. 8I. In some embodiments, the fifth folded area 81 may be greater than the fourth folded area 79, greater than the third folded area 78, greater than the second folded area 77, and/or greater than the first folded area 76.

The pants of the present invention are illustrated with the front side being initially folded into facing relation with the front side. However, in other embodiments, the pant may be initially folded with the back side in facing relation with the back side. Also, in various embodiments, the first side portion may overlay the second side portion or the second side portion may overlay the first side portion. In various embodiments, the first side portion may be folded over before the second side portion. In other embodiments, the second side portion may be folded over before the first side portion. Additionally, any of the folded configurations may be additionally folded to obtain any desirable folded configuration.

In various embodiments, the pants of the present invention may be disposed within the housing portion in any suitable orientation and any suitable alignment. In some embodiments, a package of folded pants may have a first pant with a first folded orientation and a second pant with a second folded orientation. The first folded orientation may be the same as the second orientation or may be different than the second orientation. As used herein, the term "orientation" refers to the positioning of a pant, a group of pants, or a component of a pant relative to some element of the package, the housing portion, or some component of another pant. Examples of packaging elements include, the height dimension, the width dimension, the depth dimension, the first side wall, the second side wall, the top wall, the bottom wall, the front wall, the back wall, the window region, the border region, the text, the reading direction, and the like. Examples of pant components include, the folded edges, the longitudinal direction, the transverse direction, the waist opening, the leg opening, the side seam, the waist end, the crotch end, the length, the width, the area, the side portions, the center portion, the crotch region, the waistband region, the front panel, the front waist band portion, the back panel, the back waist band portion, the crotch panel, the absorbent composite, the back sheet, the top sheet, the core, and the like.

Figure 10:
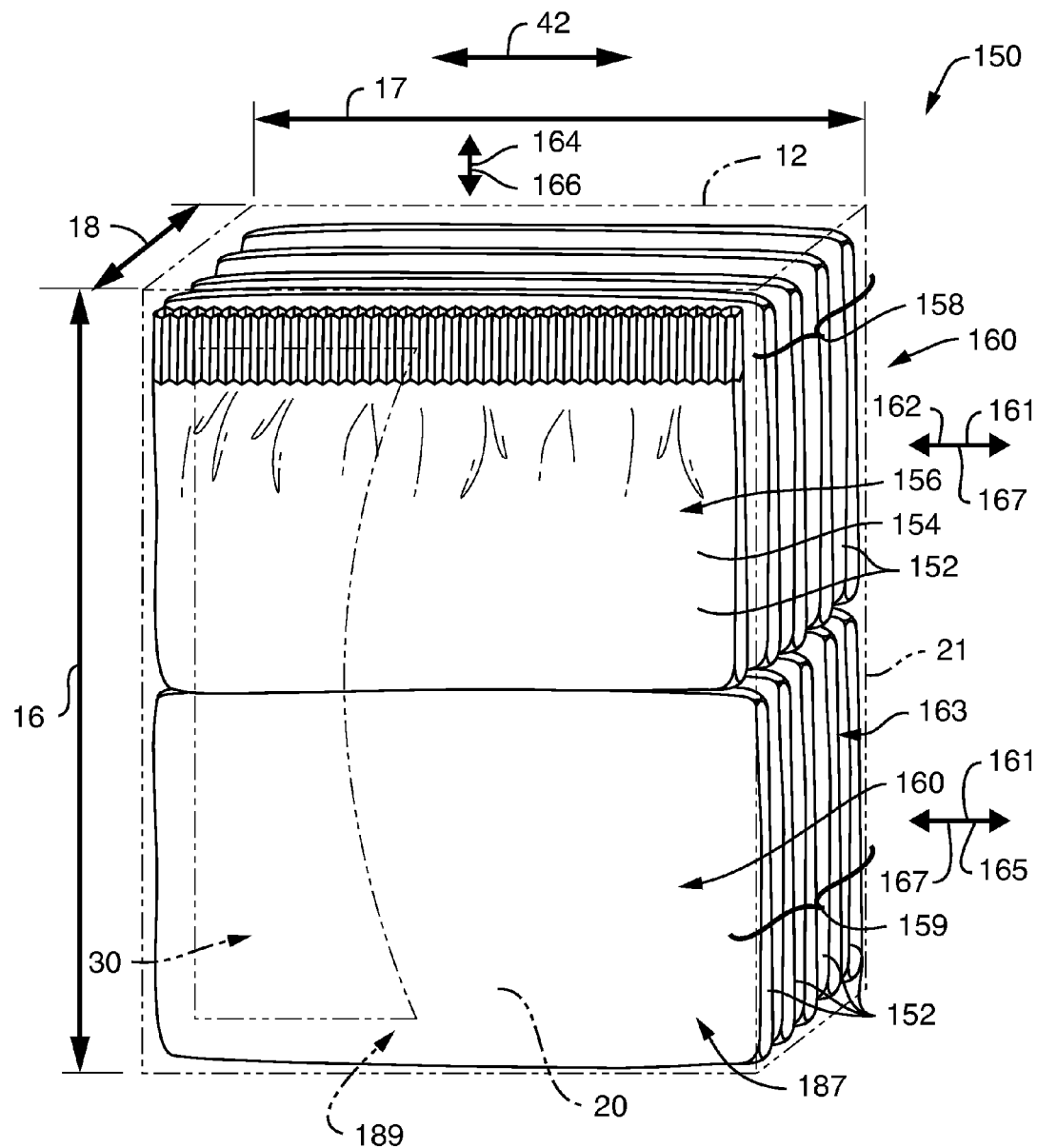
FIG. 10 representatively illustrates a perspective view of an exemplary package of folded disposable absorbent pants with the housing portion and window region in phantom to better illustrate internal features.

Referring now to FIG. 10, a package 150 of folded absorbent pants 152 is representatively illustrated. The package 150 is like those described herein and includes a housing portion 12, which defines a height dimension 16, a width dimension 17, and a depth dimension 18. The housing portion 12 includes a front wall 20 and a back wall 21, each of which extends along the width 17 and height 16 dimensions. The front wall 20 is spaced from the back wall 21 in the depth dimension 18. The front wall 20 includes a transparent window region 30. The housing portion 12, the front wall 20, the back wall 21, and the transparent window region 30 are drawn in phantom to better illustrate the location and orientation of the pants 152 contained within the package 150. Each pant 152 disposed within the housing portion 12 defines a waist opening, two leg openings, a waist end, and a crotch end like those described herein. Each pant 152 also defines a pant longitudinal direction that extends from the waist end to the crotch end and a pant transverse direction that is perpendicular to the longitudinal direction as described herein.

At least one of the pants 152 is a display pant 154 having a first folded configuration 156 and being positioned within the housing portion 12 to be at least partially visible through the transparent window region 30. A portion of the pants 152 are aligned in facing relation to define a first stack 158. Each pant 152 in the first stack 158 has a second folded configuration 160 and each pant 152 in the first stack 158 has a pant longitudinal direction 161 aligned with the other pants 152 in the first stack 158 to define a first stack longitudinal direction 162. In some embodiments, a portion of the pants are aligned in facing relation to define one or more additional stacks. For example, in FIG. 10, a portion of the pants 152 are aligned in facing relation to define a second stack 159. Each pant 152 in the second stack 159 has a third folded configuration 163 and each pant 152 in the second stack 159 has a pant longitudinal direction 161 aligned with the other pants 152 in the second stack 159 to define a second stack longitudinal direction 165.

The display pant 154 is positioned within the housing portion 12 such that the display pant longitudinal direction 164 is aligned in a first direction 166 and the first stack longitudinal direction 162 is aligned in a second direction 167 that is different than the first direction 166. In the embodiment illustrated in FIG. 10, the first direction 166 is in the height dimension 16 and the second direction 167 is in the width dimension 17. In some embodiments, the front wall 20 includes text (not illustrated) which defines a reading direction 42 aligned with the first stack longitudinal direction 162 and perpendicular to the display pant longitudinal direction 164. In this embodiment, the second stack longitudinal direction 165 also aligns with a second direction 167 and is different than the first direction 166. In the embodiment illustrated in FIG. 10, the longitudinal direction 51 of the display pant 154 is oriented in the height dimension 16 and the first stack longitudinal direction 162 and the second stack longitudinal direction 165 are oriented in the width dimension 17.

In some embodiments, the folded configuration of the display pant may be the same or may be different than the folded configuration of the pants in the first stack and/or the pants in the second stack. In some embodiments, the first folded configuration 156 of the display pant 154 is different than the second folded configuration 160 of the pants in the first stack 158 and is different than the third folded configuration 163 of the pants in the second stack 159. In various embodiments, the display pant 154, the pants in the first stack 158, and the pants in the second stack 159 may have any suitable folded configuration like those described herein. In particular, the display pant 154 of FIG. 10 has a folded configuration 156 that is similar to the folded configuration 137 illustrated in FIG. 8E. In contrast, the pants 152 in the first stack 158 and the pants 152 in the second stack 159 have a folded configuration 160 that is similar to the folded configuration 149 illustrated in FIG. 9C.

Figure 11:
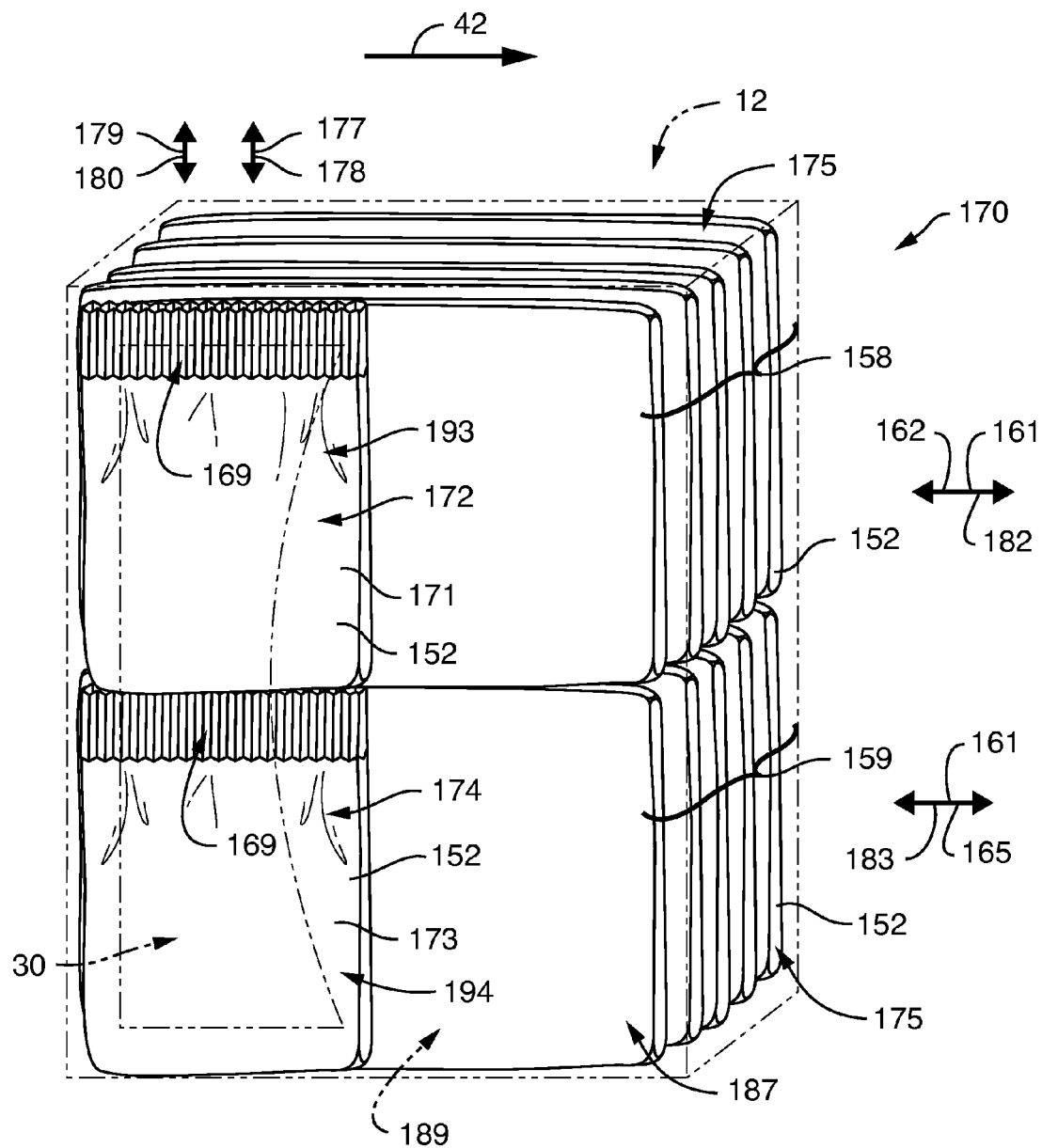
FIG. 11 representatively illustrates a perspective view of another exemplary package of folded disposable absorbent pants with the housing portion and window region in phantom to better illustrate internal features.
Figure 12:
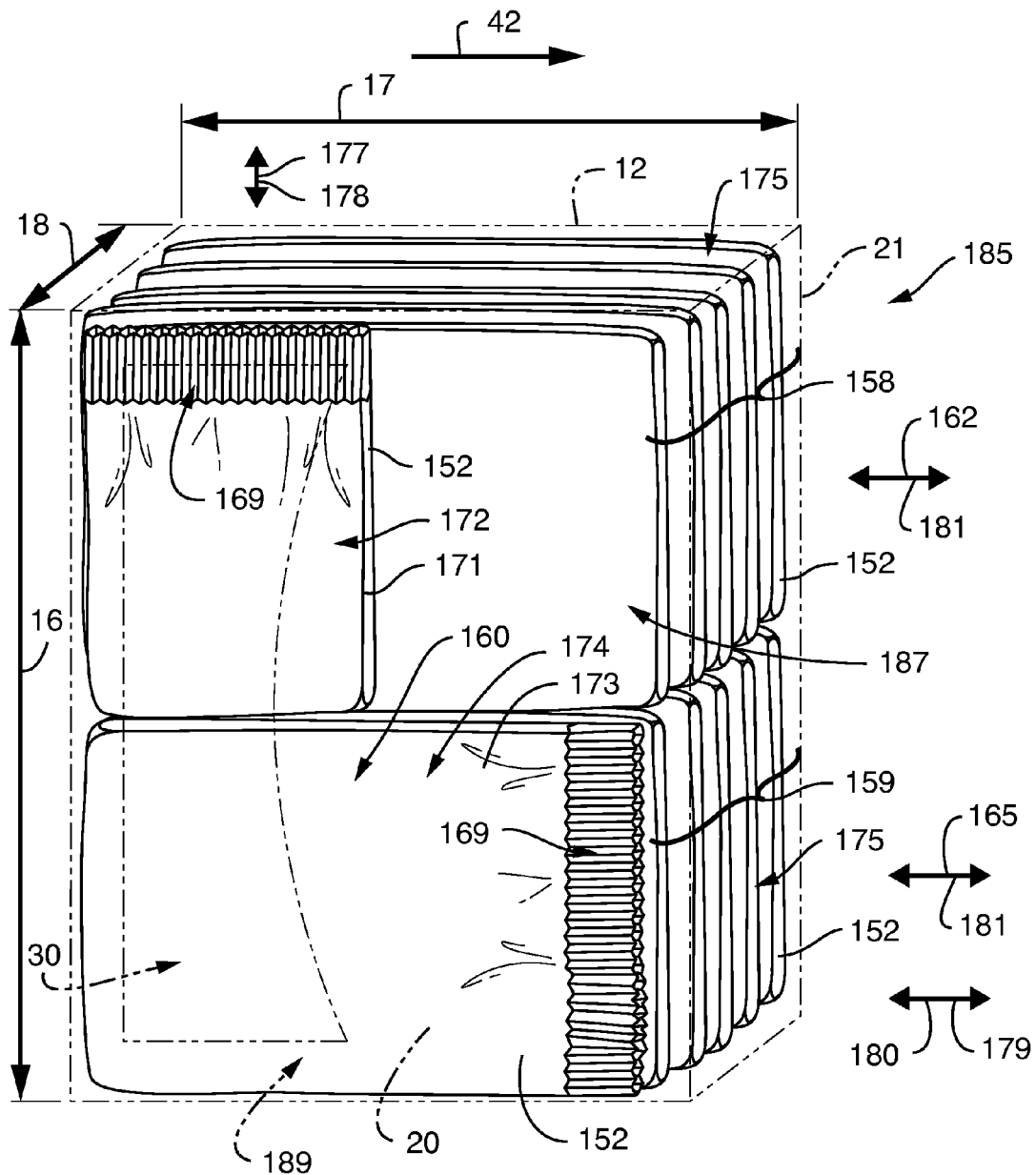
FIG. 12 representatively illustrates a perspective view of another exemplary package of folded disposable absorbent pants with the housing portion and window region in phantom to better illustrate internal features.

In various embodiments, the pants in the first stack 158 and/or the pants in the second stack 159 may have a first face plane 187 defined by the pant longitudinal direction 51 and the pant transverse direction 53, that is parallel with a second face plane 189 defined by the height dimension 16 and the width dimension 17 of the housing portion 12 (i.e., parallel with the front wall 20 and the back wall 21) as illustrated in FIGS. 10, 11, and 12. In some embodiments, the pants in the first stack and/or the pants in the second stack may have a first face plane defined by the pant longitudinal direction and the pant transverse direction that is parallel with a third face plane defined by the width dimension and the depth dimension of the housing portion (i.e., parallel with the top wall and the bottom wall) (not illustrated). In some embodiments, the pants in the first stack and/or the pants in the second stack may have a first face plane defined by the pant longitudinal direction and the pant transverse direction that is parallel with a fourth face plane defined by the length dimension and the depth dimension of the housing portion (i.e., parallel with the first side wall and the second side wall) (not illustrated). In any of these embodiments, the first display pant and/or the second display pant may have a face plane defined by the pant longitudinal direction and the pant transverse direction that is parallel with the front wall and the back wall of the housing portion. For example, referring to FIG. 11, the first display pant 171 has a face plane 193 defined by the pant longitudinal direction 177 and the pant transverse direction 182 that is parallel with the second face plane 189 of the housing portion 12. Likewise, the second display pant 173 has a face plane 194 defined by the pant longitudinal direction 177 and the pant transverse direction 183 that is parallel with the face plane 189 of the housing portion 12.

Referring still to FIG. 11, a package 170 of folded absorbent pants 152 is representatively illustrated. Likewise, FIG. 12 illustrates a package 185 of folded absorbent pants 152. The packages 170 and 185 are like those described herein and both include a housing portion 12, a height dimension 16, a width dimension 17, a depth dimension 18, a front wall 20, and a back wall 21. The housing portion 12, the front wall 20, the back wall 21, and the transparent window region 30 are drawn in phantom to better illustrate the location and orientation of the pants 152 contained within the packages 170 and 185. Each pant 152 disposed within the housing portion 12 defines a waist opening, two leg openings, a waist end, and a crotch end like those described herein. Each pant 152 also defines a pant longitudinal direction that extends from the waist end to the crotch end and a pant transverse direction that is perpendicular to the longitudinal direction as described herein. Each pant 152 also defines a waistband region 169 which abuts the waist end and which extends in the transverse direction to at least partially encircle the waist opening like those described herein.

At least one of the pants 152 is a first display pant 171 having a first folded configuration 172 and being positioned within the housing portion 12 to be at least partially visible through the transparent window region 30. In FIGS. 11 and 12, at least one of the pants 152 is a second display pant 173 having a second folded configuration 174 and is positioned within the housing portion 12 to be at least partially visible through the transparent window region 30. A portion of the pants 152 are aligned in facing relation to define a first stack 158. Each pant 152 in the first stack 158 has a third folded configuration 175 and each pant 152 in the first stack 158 has a pant longitudinal direction 161 aligned with the other pants 152 in the first stack 158 to define a first stack longitudinal direction 162. A portion of the pants 152 are aligned in facing relation to define a second stack 159. Each pant 152 in the second stack 159 has the third folded configuration 175 and each pant 152 in the second stack 159 has a pant longitudinal direction 161 aligned with the other pants 152 in the second stack 159 to define a second stack longitudinal direction 165.

In various embodiments, the first display pant and/or the second display pant has a folded configuration and is positioned within the housing portion such that the waistband region is at least partially visible through the transparent window region. For example, the package 170 of FIG. 11 illustrates both the first display pant 171 and the second display pant 173 having folded configurations and being positioned within the housing portion such that the respective waistband region 169 is partially visible through the transparent window region 30. In contrast, the package 185 of FIG. 12 illustrates only the first display pant 171 having a folded configuration and being positioned within the housing portion such that the waistband region 169 is partially visible through the transparent window region 30. The second display pant 173 has a folded configuration and is positioned within the housing portion to be partially visible through the transparent window region 30 but the waistband region 169 is not visible through the transparent window region 30.

In various embodiments, the transparent window region may include a first window and a second window wherein the first window is separated from the second window by an opaque bridge. In these embodiments, the first display pant and/or the second display pant may be visible through the first window and/or the second window. In some embodiments, the first display pant is visible only through the first window and the second display pant is visble only through the second window.

The first display pant 171 and the second display pant 173 are positioned within the housing portion 12 such that the first display pant longitudinal direction 177 aligns with a first direction 178 and the second display pant longitudinal direction 179 aligns with a second direction 180. Likewise, the first stack longitudinal direction 162 aligns with a third direction 181 and the second stack longitudinal direction 165 aligns with the third direction 181. In various embodiments, the first direction may be the same as the second direction and different than the third direction. In some embodiments, the first direction may be different than the second direction and different than the third direction. For example, in FIG. 11, the first display pant longitudinal direction 177 is aligned in a first direction 178 and the second display pant longitudinal direction 179 is aligned in a second direction 180 that is the same as the first direction but is different than the first stack longitudinal direction 162 and the second stack longitudinal direction 165. In other words, the first display pant longitudinal direction 177 and the second display pant longitudinal direction 179 are aligned with the height dimension 16 of the package 150. Also, the first stack longitudinal direction 162 and the second stack longitudinal direction 165 are aligned with the width dimension 17. In the example of FIG. 12, the first display pant longitudinal direction 177 is aligned in a first direction 178 and the second display pant longitudinal direction 179 is aligned in a second direction 180 that is different than the first direction 178. The first direction 178 is different than the first stack longitudinal direction 162 and the second stack longitudinal direction 165. In other words, the first display pant longitudinal direction 177 is aligned with the height dimension 16 of the package 150. Also, the second display pant longitudinal direction 179, the first stack longitudinal direction 162, and the second stack longitudinal direction 165 are all aligned with the width dimension 17.

In various embodiments, the package 170 or 185 may have a front wall that includes text (not illustrated) which defines a reading direction 42 aligned with the first stack longitudinal direction. In some embodiments, the reading direction 42 may also be aligned with the second display pant longitudinal direction 179 and perpendicular to the first display pant longitudinal direction 177 as illustrated in FIG. 12.

In various embodiments, the first folded configuration 172 of the first display pant 171 is different than the second folded configuration 174 of the second display pant 173 like illustrated in FIG. 12. In some embodiments, the first folded configuration 172 of the first display pant 171 is the same as the second folded configuration 174 of the second display pant 173 as illustrated in FIG. 11. In some embodiments, the first folded configuration 172 and/or the second folded configuration 174 may be the same as the third folded configuration 175. In some embodiments, the first folded configuration 172 and/or the second folded configuration 174 may be different than the third folded configuration 175. In various embodiments, the first display pant 171 and the second display pant 173 may have any suitable folded configuration like those described herein. Likewise, the pants 152 within the first stack 158 and the pants 152 within the second stack 159 may have any suitable folded configuration like those described herein.

In particular, the first display pant 171 and the second display pant 173 of FIG. 11 have a folded configuration that is similar to the folded configuration 120 illustrated in FIG. 7D. In contrast, the pants 152 in the first stack 158 and the pants 152 in the second stack 159 have a folded configuration that is similar to the folded configuration 149 illustrated in FIG. 9C. In other words, the first display pant folded configuration is the same as the second display pant folded configuration but different than the folded configurations of the pants in the first and second stacks.

Referring again to FIG. 12, the first display pant 171 has a folded configuration that is similar to the folded configuration 120 illustrated in FIG. 7D. In contrast, the second display pant 173, the pants 152 in the first stack 158, and the pants 152 in the second stack 159 have a folded configuration 160 that is similar to the folded configuration 149 illustrated in FIG. 9C. In other words, the first display pant folded configuration is different than the second display pant folded configuration and different than the folded configurations of the pants in the first and second stacks.

In various embodiments, the first display pant may have a first color and the second display pant may have a second color that is the same or is different than the first color. In some embodiments, the first display pant may have a first color and the pants in the first stack may have the first color. In some embodiments, the second display pant may have a second color different than the first color and the pants in the second stack may have the second color.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A package of folded absorbent pants, the package comprising:
    a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region;
    a plurality of absorbent pants disposed within the housing portion, each pant defining a waist opening, two leg openings, a waist end, and a crotch end, each pant defining a pant longitudinal direction that extends from the waist end to the crotch end and a pant transverse direction that is perpendicular to the longitudinal direction;
    wherein at least one of the pants is a display pant having a first folded configuration and being positioned within the housing portion to be at least partially visible through the transparent window region;
    wherein a portion of the pants are aligned in facing relation to define a first stack and wherein each pant in the first stack has a second folded configuration and the longitudinal direction of each pant in the first stack is aligned to define a first stack longitudinal direction;
    wherein the display pant is positioned within the housing portion such that the longitudinal direction of the display pant is aligned in a first direction and the first stack longitudinal direction is aligned in a second direction that is different than the first direction.

2. The package of claim 1 wherein the front wall includes text which defines a reading direction aligned with the first stack longitudinal direction and perpendicular to the display pant longitudinal direction.

3. The package of claim 2 wherein the first folded configuration is different than the second folded configuration.

4. The package of claim 3 wherein the display pant defines a first folded area in the first folded configuration and each pant in the first stack defines a second folded area in the second folded configuration that is larger than the first folded area.

5. The package of claim 4 wherein a portion of the pants are aligned in facing relation to define a second stack and wherein each pant in the second stack has a third folded configuration and the longitudinal direction of each pant in the second stack is aligned to define a second stack longitudinal direction.

6. The package of claim 5 wherein at least one of the pants is a second display pant having a fourth folded configuration and being positioned within the housing portion to be at least partially visible through the transparent window region.

7. The package of claim 6 wherein the transparent window region comprises a first window and a second window, wherein the first window is separated from the second window by an opaque bridge and wherein the first display pant is positioned within the housing portion to be at least partially visible through the first window and the second display pant is positioned within the housing portion to be at least partially visible through the second window.

8. The package of claim 3 wherein the display pant further defines a waistband region which abuts the waist end and which extends in the transverse direction to at least partially encircle the waist opening and wherein at least a portion of the waistband region is visible through the transparent window region.

9. The package of claim 3 wherein the pants in the first stack are oriented within the housing portion such that the plane defined by the longitudinal direction and the lateral direction of the pants in the first stack is parallel with the front wall.

10. A package of folded absorbent pants, the package comprising:
- a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region;
- a plurality of absorbent pants disposed within the housing portion, each pant defining a waist opening, two leg openings, a waist end, and a crotch end, each pant defining a pant longitudinal direction that extends from the waist end to the crotch end and a pant transverse direction that is perpendicular to the longitudinal direction, each pant further defining a waistband region which abuts the waist end and which extends in the transverse direction to at least partially encircle the waist opening;
- wherein at least one of the pants is a first display pant having a first folded configuration and being positioned within the housing portion such that the waistband region is at least partially visible through the transparent window region;
- wherein at least one of the pants is a second display pant having a second folded configuration and being positioned within the housing portion to be at least partially visible through the transparent window region but the waistband region is not visible through the transparent window region;
- wherein a portion of the pants are aligned in facing relation to define a first stack and wherein each pant in the first stack has a third folded configuration and the longitudinal direction of each pant in the first stack is aligned to define a first stack longitudinal direction;
- wherein a portion of the pants are aligned in facing relation to define a second stack and wherein each pant in the second stack has a fourth folded configuration and the longitudinal direction of each pant in the second stack is aligned to define a second stack longitudinal direction;
- wherein the first display pant and the second display pant are positioned within the housing portion such that the longitudinal direction of the first display pant is aligned with a first direction, the longitudinal direction of the second display pant is aligned with a second direction that is different than the first direction, and the longitudinal direction of the first stack is aligned with the second direction.

11. The package of claim 10 wherein the front wall includes text which defines a reading direction aligned with the first stack longitudinal direction and the second display pant longitudinal direction and perpendicular to the first display pant longitudinal direction.

12. The package of claim 11 wherein the pants in the first stack are positioned such that the plane defined by the longitudinal direction and the lateral direction is parallel with the front wall and wherein the pants in the second stack are positioned such that the plane defined by the longitudinal direction and the lateral direction is parallel with the front wall.

13. The package of claim 12 wherein the first display pant overlays the first stack and wherein the second display pant overlays the second stack.

14. The package of claim 13 wherein the transparent window region comprises a first window and a second window, wherein the first window is separated from the second window by an opaque bridge and wherein the first display pant is positioned within the housing portion to be at least partially visible through the first window and the second display pant is positioned within the housing portion to be at least partially visible through the second window.

15. The package of claim 14 wherein the first display pant has a first color and the second display pant has a second color different than the first color.

16. The package of claim 10 wherein the first folded configuration is the same as the second folded configuration and different than the third folded configuration.

17. The package of claim 10 wherein the second folded configuration is the same as the third folded configuration and different than the first folded configuration.

18. The package of claim 17 wherein the first display pant defines a first folded area in the first folded configuration and the second display pant defines a second folded area in the second folded configuration that is larger than the first folded area.

19. A package of folded absorbent pants, the package comprising:
- a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region, the front wall also comprises text that defines a reading direction that is aligned with the width dimension of the housing portion;
- a plurality of absorbent pants disposed within the housing portion, each pant defining a waist opening, two leg openings, a waist end, and a crotch end, each pant defining a pant longitudinal direction that extends from the waist end to the crotch end and a pant transverse direction that is perpendicular to the longitudinal direction, each pant further defining a waistband region which abuts the waist end and which extends in the transverse direction to at least partially encircle the waist opening;
- wherein at least one of the pants is a first display pant having a first folded configuration and being positioned within the housing portion and being at least partially visible through the transparent window region;
- wherein at least one of the pants is a second display pant having a second folded configuration and being positioned within the housing portion and being at least partially visible through the transparent window region;
- wherein a portion of the pants are aligned in facing relation to define a first stack and wherein each pant in the first stack has a third folded configuration and the longitudinal direction of each pant in the first stack is aligned to define a first stack longitudinal direction;
- wherein a portion of the pants are aligned in facing relation to define a second stack and wherein each pant in the second stack has a fourth folded configuration and the longitudinal direction of each pant in the second stack is aligned to define a second stack longitudinal direction;

wherein the first display pant and the second display pant are positioned within the housing portion such that the longitudinal direction of the first display pant is aligned with a first direction, the longitudinal direction of the second display pant is aligned with a second direction that is different than the first direction, the longitudinal direction of the first stack is aligned with the second direction, and the longitudinal direction of the second stack is aligned with the second direction; and wherein the first folded configuration is different than the second folded configuration, the third folded configuration, and the fourth folded configuration.

20. The package of claim 19 wherein the first display pant is positioned within the housing portion such that the waistband region is at least partially visible through the transparent window region and wherein the second display pant is positioned within the housing portion such that the waistband region is not visible through the transparent window region.

* * * * *